(12) United States Patent
Poulos et al.

(10) Patent No.: US 12,167,915 B2
(45) Date of Patent: Dec. 17, 2024

(54) BIPOLAR NERVE STIMULATION/MONITORING CUFF

(71) Applicant: Retropsoas Technologies, LLC, Frontenac, MO (US)

(72) Inventors: Nicholas Poulos, Frontenac, MO (US); James Cupp, Indiana, PA (US)

(73) Assignee: Retropsoas Technologies, LLC, Frontenac, MO (US)

( * ) Notice: Subject to any disclaimer, the term of this patent is extended or adjusted under 35 U.S.C. 154(b) by 0 days.

(21) Appl. No.: 18/651,145

(22) Filed: Apr. 30, 2024

(65) Prior Publication Data

US 2024/0350064 A1    Oct. 24, 2024

Related U.S. Application Data

(63) Continuation of application No. PCT/US2024/023898, filed on Apr. 10, 2024.
(Continued)

(51) Int. Cl.
*A61B 5/294* (2021.01)
*A61B 5/251* (2021.01)
*A61B 5/263* (2021.01)

(52) U.S. Cl.
CPC .............. *A61B 5/294* (2021.01); *A61B 5/251* (2021.01); *A61B 5/263* (2021.01)

(58) Field of Classification Search
CPC ....... A61B 5/293; A61B 5/294; A61B 5/4893; A61B 5/6836; A61B 5/6838;
(Continued)

(56) References Cited

U.S. PATENT DOCUMENTS

| 4,612,936 A | * | 9/1986 | Yamaguchi | ............ | A61B 5/274 |
| | | | | | 600/386 |
| 5,013,069 A | * | 5/1991 | Hardin | ................... | G09B 19/22 |
| | | | | | 283/49 |

(Continued)

OTHER PUBLICATIONS

Atlantic Gasket Corportaion, Typical Properties of Style AG80HS 80 Durometer High Strength Grade Silicone. https://web.archive.org/web/20220515000000*/https://www.atlanticgasket.com/gasket-manufacturing/types-of-gaskets/high-strength-silicone-80-spec.html (Year: 2022).*

(Continued)

*Primary Examiner* — Eun Hwa Kim
(74) *Attorney, Agent, or Firm* — Sandberg Phoenix & von Gontard P.C.

(57) ABSTRACT

An electrode assembly (preferably in the form of a nerve cuff) comprises a base with first and second arms extending from opposite sides of the base, and which, in combination, define an arc. First and second electrically conductive electrodes extend along the inner surface of the first and second arms. Each electrode can comprise a single length of foil can or can comprise multiple discrete foil segments. The foils are electrically isolated from each other. Electrical wires, which are in electrical communication with the each of the foils, extend from the nerve cuff and are adapted to be electrically connected to a signal monitor. When the nerve cuff is applied to a nerve, the foils, in combination, substantially surround the nerve, with the first and second electrodes being on opposite sides of the nerve from each other. Also disclosed is a method of using the nerve cuff to monitor a nerve during a lumbar spinal surgery while the patient is anesthetized and paralyzed.

23 Claims, 13 Drawing Sheets

Related U.S. Application Data

(60) Provisional application No. 63/496,945, filed on Apr. 18, 2023.

(58) Field of Classification Search
CPC ... A61B 5/6876; A61B 5/6868; A61B 5/6877; A61B 5/6884; A61N 1/0556; Y10T 24/44538; Y10T 24/44923
See application file for complete search history.

(56) References Cited

U.S. PATENT DOCUMENTS

| | | | |
|---|---|---|---|
| 5,375,594 A | 12/1994 | Cueva | |
| 6,308,105 B1 * | 10/2001 | Duysens | A61N 1/0551 607/116 |
| 7,177,702 B2 | 2/2007 | Wallace et al. | |
| 7,803,021 B1 | 9/2010 | Brase | |
| 7,996,092 B2 * | 8/2011 | Mrva | A61N 1/0556 607/118 |
| 8,192,426 B2 | 6/2012 | Stern et al. | |
| 8,983,626 B2 | 3/2015 | Zarembo et al. | |
| 9,114,250 B2 * | 8/2015 | True | A61N 1/0556 |
| 9,283,379 B2 | 3/2016 | True et al. | |
| 9,320,889 B2 | 4/2016 | Jackson et al. | |
| 9,572,976 B2 | 2/2017 | Howard et al. | |
| 10,182,731 B2 * | 1/2019 | Su | A61N 1/048 |
| 10,485,969 B2 | 11/2019 | Govea et al. | |
| 10,729,342 B2 | 8/2020 | Cantwell et al. | |
| 11,259,737 B2 | 3/2022 | Taylor | |
| 2006/0271137 A1 | 11/2006 | Stanton-Hicks | |
| 2010/0174147 A1 | 7/2010 | Miles et al. | |
| 2010/0305674 A1 | 12/2010 | Zarembo et al. | |
| 2015/0230749 A1 | 8/2015 | Gharib et al. | |
| 2018/0028820 A1 | 2/2018 | Nageri | |
| 2019/0060641 A1 | 2/2019 | Schüttler et al. | |
| 2019/0321644 A1 * | 10/2019 | Maharbiz | A61B 5/6877 |
| 2021/0007624 A1 * | 1/2021 | Clay | A61B 5/282 |
| 2022/0378351 A1 * | 12/2022 | Cantwell | A61B 5/4041 |

OTHER PUBLICATIONS

Ruckenstein et al; Advantages of a New, Atraumatic, Self-Retaining Electrod for Direct Cochlear Nerve Monitoring, Skull Base Surgery, vol. 7, No. 2, 1997, pp. 69-75 (7 pages), doi: 10.1055/s-2008-1058611.

* cited by examiner

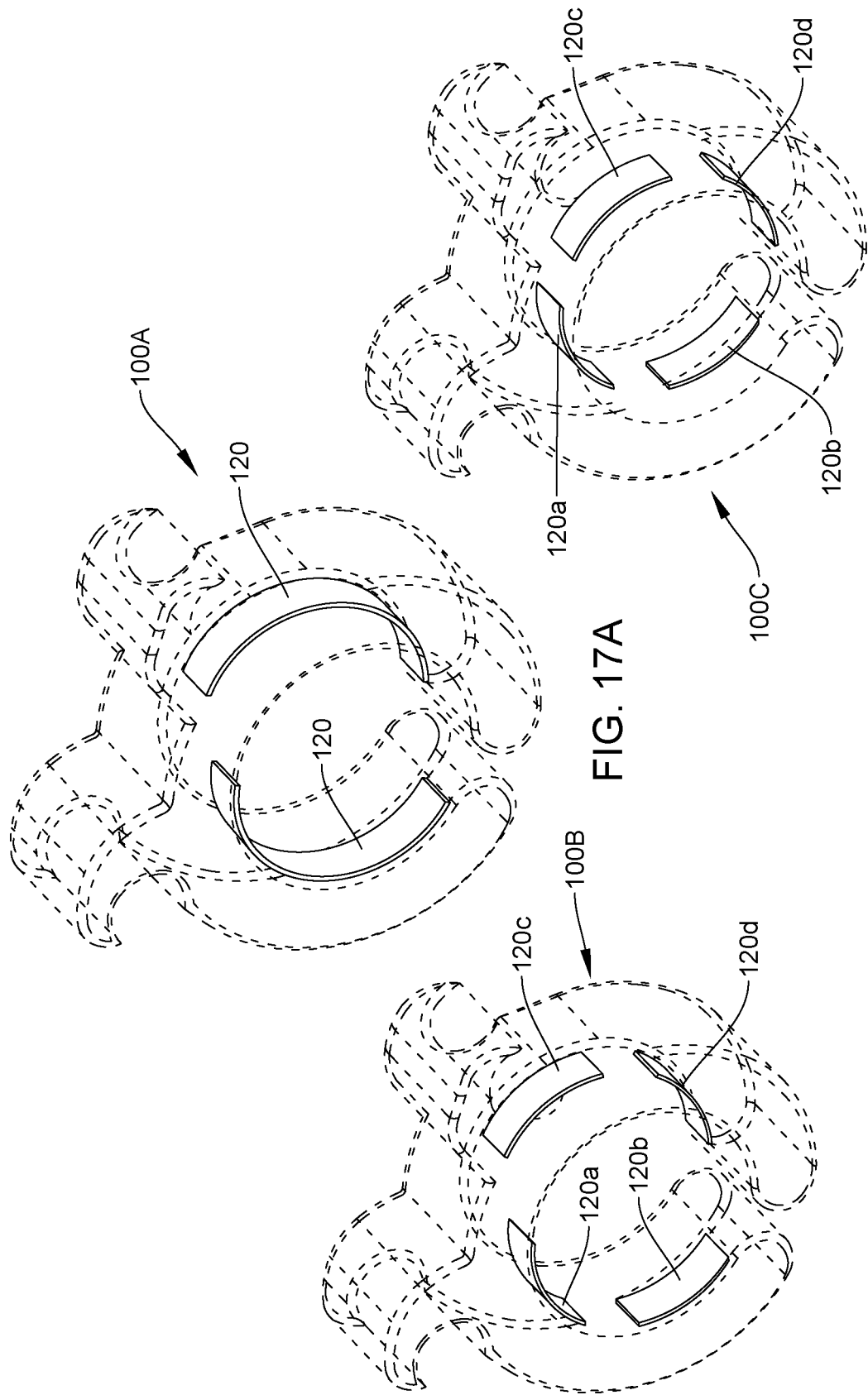

BIPOLAR NERVE STIMULATION/MONITORING CUFF

CROSS-REFERENCE TO RELATED APPLICATIONS

This application is a continuation of International App. No. PCT/US2024/023898, filed Apr. 10, 2024 which claims priority to U.S. App. No. 63/496,945 filed Apr. 18, 2023, entitled "Bipolar Nerve Stimulation/Monitoring Cuff Electrode", the contents (text, drawings, and claims) of both said applications being incorporated herein by reference.

STATEMENT REGARDING FEDERALLY SPONSORED RESEARCH OR DEVELOPMENT

Not Applicable.

BACKGROUND

This application relates to an electrode for use during spinal surgery, and in particular to a nerve cuff, and to a method of using the nerve cuff to monitor a nerve during spinal surgery, and in particular to lumbar nerve root monitoring.

FIGS. 1A-2 illustratively show a spinal column C. The spinal column C comprises vertebrae V separated by fibrocartilaginous discs D which form a protective column through which the spinal cord S passes. Nerves N extend from the spinal cord S between vertebrae V to ultimately reach all parts of the body. As shown schematically in FIGS. 1A-B, the nerves extending from the spinal cord comprise a dorsal root 5 and ventral root 6 which are encased in arachnoid matter 9, which in turn is surrounded by dura mater 10. The dorsal and ventral roots as encased by the arachnoid matter and dura matter define a spinal nerve root 12 which exits the spinal cord between adjacent vertebrae. With reference to the lumbar section of the spine, as shown in FIG. 2, the nerve roots enter the lumbar plexus where they split, converge, and combine in the psoas muscle, and then divide further into peripheral nerves.

In the nerve root, as seen in FIG. 1A, the dorsal root 5 and the ventral root 6, comprise a sensory nerve bundle and a motor nerve bundle, respectively, which are distinct and separate from each other, with the sensory bundle being located dorsally and the motor bundle being located ventrally. As is known, the motor nerve bundle sends signals from the brain to muscle, and the sensory nerve bundle sends signals from the muscle, organs, and soft tissues to the brain. In the plexus, the sensory and motor bundles become intermingled and become difficult to distinguish. The nerve root is the only portion of the nervous system where the motor and sensory nerve bundles are distinctly separate and individually accessible.

During spinal surgery, as shown schematically in FIG. 3, the nerve at the surgical site can be held out of the way by means of a retractor. The act of holding the nerve out of the way will cause the retractor to apply pressure to the nerve which can irritate or compress the nerve. So that injury to the nerve can be minimized, the nerves at the surgical site can be monitored. There are currently several methods to monitor the nerve as part of an electrical network. In one method, a needle (a scalp electrode) can be placed in the scalp overlying the motor portion of the brain and a separate needle (a muscle electrode) can be placed directly in a muscle or in close proximity to the muscle targeted by the nerve to be monitored. The scalp electrode, nerve, and muscle electrode define an electrical network, and signals from the scalp electrode to the muscle electrode can be monitored and measured. The brain can be intermittently stimulated via the scalp electrode, and signals, in the form of muscle contractions/action potentials, can be documented. During surgery, the network is monitored to detect changes in the signal from a base signal. Deviation from the base signal can indicate that the nerve is being irritated or injured, and that the retractor should be moved or tension or compression on the nerve should be reduced. In an alternative method, a needle electrode can be placed in proximity to a peripheral nerve (for example, in an arm or leg) and a separate needle (a scalp electrode) can be placed in the scalp over the sensory portion of the brain. The peripheral needle electrode can be periodically stimulated and changes in the amplitude and latency in the signal arriving at the scalp electrode can be measured. Changes over a baseline signal would imply potential nerve root injury and that corrective action should be taken by the surgeon regarding management of the retractor.

Direct monitoring of the lumbar spinal nerve root function is also known. This involves the intermittent application of a probe touching the nerve and measuring downstream signal changes in the muscle. There are other, less popular monitoring techniques known to spinal surgeons.

All of the aforementioned monitoring techniques are limited by specificity, sensitivity, and/or anatomical/surgical constraints which, due to the unique anatomy of the exiting lumbar nerve root, potentially render some or all techniques suboptimal or even useless for monitoring the exiting lumbar nerve root during surgery. In particular, the current standard of intermittent monitoring requires that the surgeon temporarily stop the procedure to check the status of the lumbar nerve root in question. There is currently no device available which is in continuous contact with the lumber nerve root to allow for much more frequent monitoring of the lumbar nerve root.

The analysis of signal changes in the exiting nerve root can further be confounded by electrode devices and systems not specifically designed for the exiting lumbar nerve root. There are currently several types of nerve stimulation devices that are available. Broadly, there are implantable or removable devices. An example of an implantable device is disclosed in U.S. Pat. No. 9,283,379. The nerve stimulation device disclosed therein comprises a generally circular cuff designed to be positioned about a nerve. A single electrode is positioned within the nerve cuff body to be in electrical communication with the nerve such that when the electrode is activated, the nerve will be stimulated. This electrode is connected to an implanted subcutaneous generator device that cannot interact with a surgeon in real time, and thus this electrode cannot be used for monitoring or recording the nerve during a surgical procedure.

US Pub. No. 20060271137 and U.S. Pat. No. 10,485,969 both disclose implantable stimulators which can be applied, for example, to a leg nerve, to treat chronic pain. These nerve stimulators both comprise an elongate body designed to surround a length of a nerve, and each of the stimulators has a plurality of discrete electrodes formed in an axially extending array which are positioned to be located close to, or in contact with, the nerve to be stimulated. Pulse generators generate electrical pulses that are delivered to the nerve via the devices. Much like the device described in U.S. Pat. No. 9,283,379 above, these two devices are implanted programmed devices that operate autonomously, and are not designed to enable a surgeon to interact with them in real time during an operation U.S. Pat. No. 6,308,105, discloses an implantable nerve stimulator in the form of a split ring with discrete electrodes positioned around the interior of the ring. This is yet another implanted programmed device that operates autonomously with similar limitations raised previously.

U.S. Pat. No. 10,729,342, discloses a split ring removable electrode assembly for use mainly in stimulating nerves, and potentially for monitoring or recording nerves. The Cantwell device comprises a somewhat elongate, generally semi-circular body having a pair of electrodes which are connected to separate electrical leads. The electrodes are arranged longitudinally along an inner surface of the body, and thus, extend parallel to (longitudinally along) the nerve about which the nerve cuff is positioned. Due to the size of the device, the two electrodes are close together and arranged in an axially extending line, and thereby make bipolar recording challenging. Further, the assembly disclosed in this patent is provided with large ears or tabs, extending significantly beyond the outer surface of the semi-cylindrical body of the device to which they connect. These ears are used to open the body of the device for application to a nerve. The size of these ears renders the device difficult to use in a lumbar spinal surgery, as they will obstruct access to the surgical site and obscure relevant anatomy. Additionally, the large size of the ears will likely interfere with a retractor blade further limiting use of the device, especially if the target nerve is in close proximity to the retractor blade.

U.S. Pat. No. 5,375,594, discloses a removable electrode cuff that is generally semi-circular with outwardly projecting grasping portions on the surface of the arcuate cuff. The nerve cuff defines an arc of only slightly more than 180° so as not to interfere with easy placement and removal of the device. To facilitate placement and removal, the device has large grasping members which can be squeezed together to open the semi-circular device. Rather than having discrete electrodes, the device includes a single conductive silver strip which engages the nerve to be monitored. The conductive strip is connected to a conventional monitoring system via a wire. Ultimately this device has a monopolar configuration making it useful for recording nerve signals, but of limited value for stimulation of the nerve. Current spread is inevitable with monopolar stimulation with expected noise and loss of specificity exacerbated by close proximity of nontargeted nerves.

All the foregoing devices either are not suited for stimulating and/or monitoring nerves during a lumbar spinal surgery or have drawbacks rendering them difficult to use.

SUMMARY

Briefly stated, an electrode assembly comprises at least one first electrode and at least one electrical wire adapted to be electrically connected to a signal monitor which in turn is adapted to generate an electrical pulse and to monitor return signals. The at least one electrical wire is in electrical communication with the at least one electrode. The electrode assembly is sized and shaped to be received in a surgical incision during a spinal surgery and to be removably positioned about a lumbar nerve root during the spinal surgery. The electrode assembly is shaped, configured, and adapted to maintain the at least one electrode in continuous electrical communication with the lumbar nerve root throughout the spinal surgery.

In accordance with an aspect of the electrode assembly, the electrode assembly comprises at least one second electrode spaced from the at least one first electrode, with the electrode assembly being configured such that when the electrode assembly is positioned about the nerve root, the at least one first electrode and the at least one second electrode are circumferentially spaced about the lumbar nerve root.

In accordance with an aspect of the electrode assembly, the electrode(s) comprise(es) an electrically conductive foil, and if the electrode assembly comprises at least two electrodes, the electrodes are electrically isolated from each other.

In accordance with an aspect of the electrode assembly, the electrodes comprise or are made from platinum.

In accordance with an aspect of the electrode assembly, the electrode assembly comprises a body having a base and first and second arms extending from opposite sides of the base. The base and arms, which are formed from an electrically insulating material, define an inner surface. The arms each comprise a fixed end adjacent the base and a free end remote from the base. The arms and/or base are sized so as to be flexible such that the electrode assembly is moveable between a relaxed position and an open position, wherein in the open position, the arms define a gap between their free ends sized to fit over a lumbar nerve root. The body has a radial width measured along an axial plane which passes through the arms and an axial width measured in a plane that is generally perpendicular to the radial width. The at least one first electrode is positioned on an inner surface of the first arm. If the assembly comprises the at least one second electrode, the at least one second electrode is positioned in the inner surface of the second arm.

In accordance with an aspect of the electrode assembly, each arm comprises one electrode, and wherein the electrodes of the first and second arms are positioned in a common axial plane or are positioned in different axial planes.

In accordance with an aspect of the electrode assembly, each arm comprises two or more electrodes, and wherein the electrodes of the arms are positioned in a common axial plane or are positioned in different axial planes.

In accordance with an aspect of the electrode assembly, the two or more electrodes of a single arm are all positioned in the same axial plane or are positioned in different axial planes.

In accordance with an aspect of the electrode assembly, when each arm comprises a single electrode, with each the electrode defining an arc of between 120° and 140°, preferably between 125° and 135°, and preferably about 130°.

In accordance with an aspect of the electrode assembly, the inner surface of the body defines an arc of at least 270°.

In accordance with an aspect of the electrode assembly, the arms have an annular width of about 1-3 mm, and preferably about 2 mm, and preferably wherein the body defines an inner diameter of 3-10 mm, preferably about 3-8 mm, more preferably about 4 mm.

In accordance with an aspect of the electrode assembly, wherein the electrode assembly further comprises a main spring contained within at least the first and second arms, and preferably wherein the main spring comprises a single spring which extends through both the first and second arms and the base of the body.

In accordance with an aspect of the electrode assembly, the electrode assembly comprises an electrical insulator positioned between the electrodes and the main spring.

In accordance with an aspect of the electrode assembly, the electrical insulator has an axial width equal to or greater than an axial width of the main spring.

In accordance with an aspect of the electrode assembly, the electrical insulator comprises a polymer layer, preferably a polyimide, applied to at least the inner surface of the main spring, and wherein the insulating layer optionally covers free ends of the main spring and a portion of an outer surface of the main spring at ends of the main spring.

In accordance with an aspect of the electrode assembly, wherein the main spring comprises a leaf spring, the leaf spring preferably having a thickness of about 7 mils.

In accordance with an aspect of the electrode assembly, the electrode assembly further includes first and second spaced apart grasping arms extending from opposite sides of the base; the grasping arms being positioned on the base, such that by urging the grasping arms together toward each other, the electrode assembly will be moved from its relaxed position to its open position.

In accordance with an aspect of the electrode assembly, wherein the grasping arms are sized and shaped such that the distance between outer surfaces of the grasping arms is less than, or equal to, the side-to-side width of the body of the electrode assembly.

In accordance with an aspect of the electrode assembly, wherein the electrode assembly includes a grip spring member extending through each of the grasping arms, preferably wherein each the grip spring member is fixed to the main spring.

In accordance with an aspect of the electrode assembly, the electrode assembly further includes a connector at an end of each lead, the connector being color coded; wherein the electrode assembly includes indicia indicating the connector to which at least one the electrodes is electrically connected; wherein the indicia is preferably positiononed on the grasping arm or the arm of the body of the electrode assembly with which the electrode is associated; and wherein the indicia preferably comprises a marking or coloration on the grasping arm or body arm.

In accordance with an aspect of the electrode assembly, wherein the electrode assembly body is sufficiently flexible such that a nerve surrounded by the electrode assembly body can pop out of the electrode assembly body through the gap if the electrode assembly is dislodged during a surgical procedure.

In accordance with an aspect of the electrode assembly, wherein at least the arms are formed from 80 durometer silicone.

In accordance with another aspect, a method of monitoring a nerve during lumbar spinal surgery is disclosed. Briefly, the method comprises:
  positioning an electrode assembly adjacent an exiting lumbar nerve root; the electrode assembly comprising at least one electrode and at least one electrical wire adapted to be electrically connected to a signal monitor adapted to generate an electrical pulse and to monitor return signals; the at least one electrical wire being in electrical communication with the at least one electrode; the electrode assembly being sized and shaped to be received in a surgical incision during a lumbar spinal surgery and to be removably positioned about a lumbar nerve root during the spinal surgery; the electrode assembly being shaped, configured, and adapted to maintain the at least one electrode in continuous electrical communication with the lumbar nerve root throughout the spinal surgery;
  periodically generating an electrical pulse and transmitting the electrical pulse to the nerve via the at least one electrode;
  receiving return signals from the nerve at the electrode in response to the periodically generated electrical pulses;
  monitoring the return signals for changes in the return signal indicative of irritation or potential damage to the nerve; and
  removing the electrode assembly from the lumbar nerve root at the conclusion of the procedure.

In accordance with an aspect of the method, the electrode assembly comprises the electrode assembly having a body with arms, as described above.

The exiting lumbar spinal nerve root of the nerve comprises a sensory nerve bundle and a motor nerve bundle, the sensory nerve bundle and motor nerve bundle being separate and distinct from each other. The method can take advantage of this anatomical feature. Thus, in accordance with an aspect of the method, the step of positioning the electrode assembly comprises placing the electrode assembly about the nerve root such that one of the at least one first and second electrodes is in electrical communication with the sensory nerve bundle and the other of the at least one first and second electrodes is in electrical communication with the motor nerve bundle.

In accordance with an aspect of the method, the step of positioning the electrode assembly comprises placing the electrode assembly about the lumbar nerve root such that the at least one first electrode is in electrical communication with a first portion of the neve and the at least one second electrode is in electrical communication with a second portion of the nerve circumferentially spaced from the first portion, wherein one of the electrodes is a reference or inactive electrode and the other of the electrodes is an active electrode.

In accordance with an aspect of the method, the monitoring method is carried out while the patient is not paralyzed during the surgical procedure.

In accordance with an aspect of the method, the monitoring method is carried out while the patient is substantially anesthetically relaxed or paralyzed during the surgical procedure.

In accordance with an aspect of the method, the lumbar nerve root is substantially continuously stimulated for monitoring purposes or stimulated intermittently.

In accordance with an aspect of the method, the lumbar nerve root is substantially continuously recorded for monitoring purposes or recorded intermittently.

In accordance with an aspect of the method, the lumbar spinal nerve root comprises a sensory nerve bundle and a motor nerve bundle, the sensory and motor nerve bundles being separate and distinct from each other; the method further comprising:
  positioning a remote electrode on one of the patient's scalp, a limb of the patient, or on the patient's torso; the remote electrode being in electrical communication with the signal monitor;
  generating nerve stimulating pulses at one of the remote electrode and the electrode assembly, and transmitting the stimulating pulses to the nerve;
  receiving a signal in response to the nerve stimulating pulse at the other of the electrode assembly and remote electrode; and
  monitoring the return signal for changes in the signal indicative of irritation or potential damage to the nerve.

In accordance with an aspect of the method, the method of monitoring comprises one of the following paradigms:
  1. Brain (stimulate)-electrode assembly (record)
  2. Dorsal spine (stimulate)-electrode assembly (record)
  3. Peripheral nerve (stimulate)-electrode assembly (record)
  4. Electrode assembly (stimulate)-muscle (record)

5. Electrode assembly (stimulate)-brain (record)

6. Electrode assembly (stimulate)-dorsal spine (record)

In accordance with an aspect of the method, when the monitoring method comprises one of the "dorsal spinal (stimulate)-electrode assembly (record)" paradigm and the "electrode assembly (stimulate)-dorsal spine (record)" paradigm, wherein the dorsal spine electrodes further comprise deep subfascial needle electrodes which are electronically linked and are inserted to be proximate the dorsal roof of the intervertebral foramen of the spine.

In accordance with an aspect of the method, the deep subfascial needle electrodes are inserted bilaterally paramidline just lateral to the pars interarticularis at the T12-L1 level to a depth proximate the dorsal roof of the foramen.

In accordance with an aspect of the method, one of the first and second electrodes is positioned to be in electrical communication only with the sensory nerve bundle and the other of the first and second electrodes is positioned to be in electrical communication with only the motor nerve bundle; whereby the step of monitoring the return signal comprises monitoring the return signal received from the motor nerve bundle or the sensory nerve bundle.

BRIEF DESCRIPTION OF THE DRAWINGS

FIGS. 17A-C are perspective views of a cuff having alternative electrode configurations.

Corresponding reference numerals will be used throughout the several figures of the drawings.

DETAILED DESCRIPTION

Figure 1A:
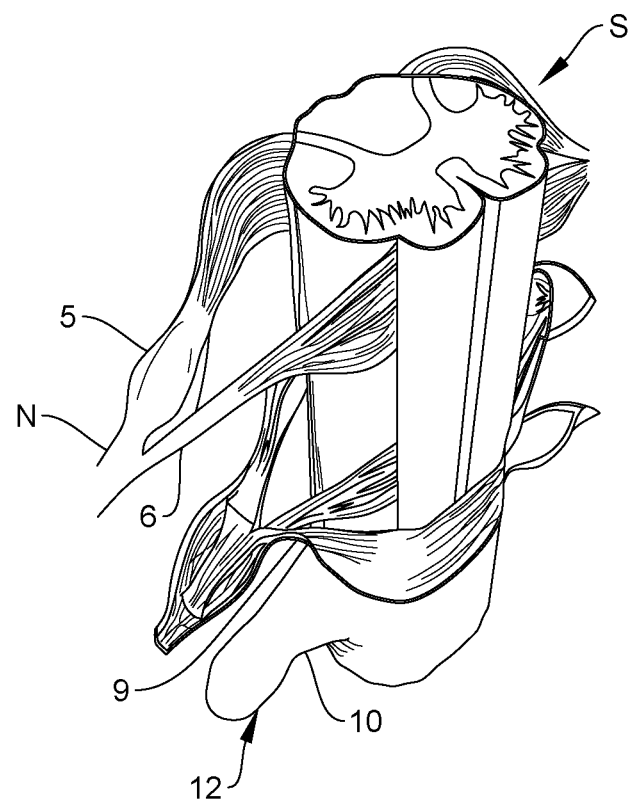
FIG. 1A is a schematic of a portion of a spinal cord with nerves extending therefrom illustratively showing spinal nerve root anatomy.
Figure 1B:
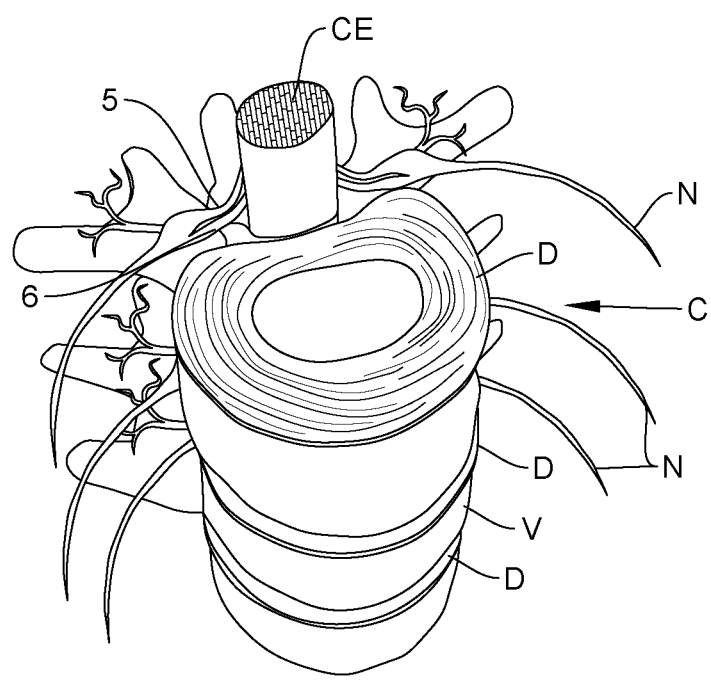
FIG. 1B is a cross-sectional schematic of a cauda equina and a spinal column.
Figure 2:
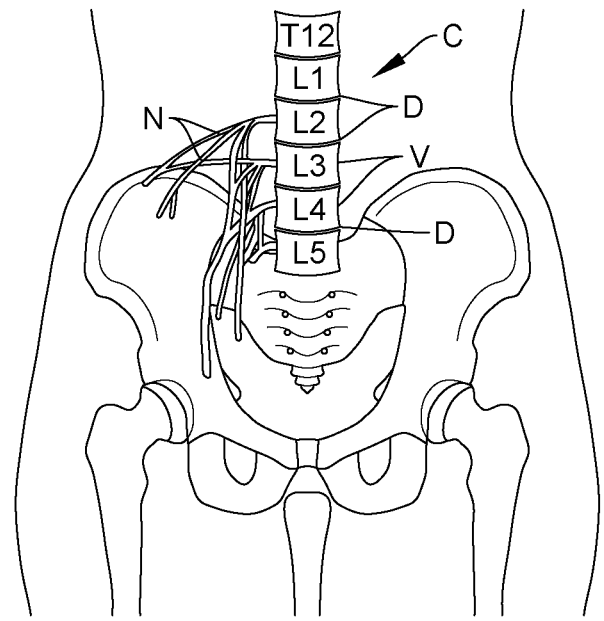
FIG. 2 is a schematic drawing of a lumbar region of a spinal column illustratively showing the lumbar spinal nerve root, lumbar plexus, and origin of peripheral nerves.
Figure 3:
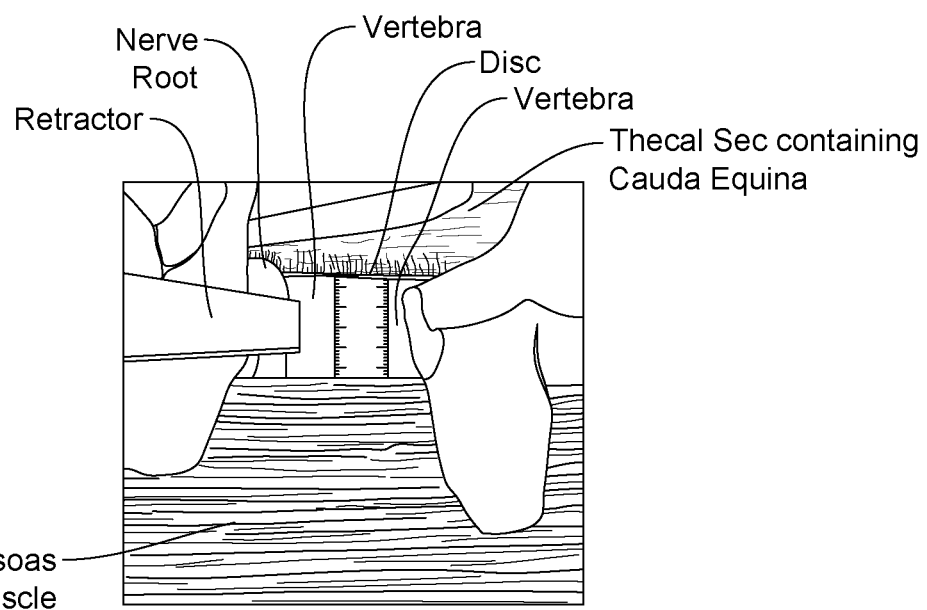
FIG. 3 is a schematic view of a surgical site during spinal surgery, such as a lumbar spinal surgery.
Figure 4A:
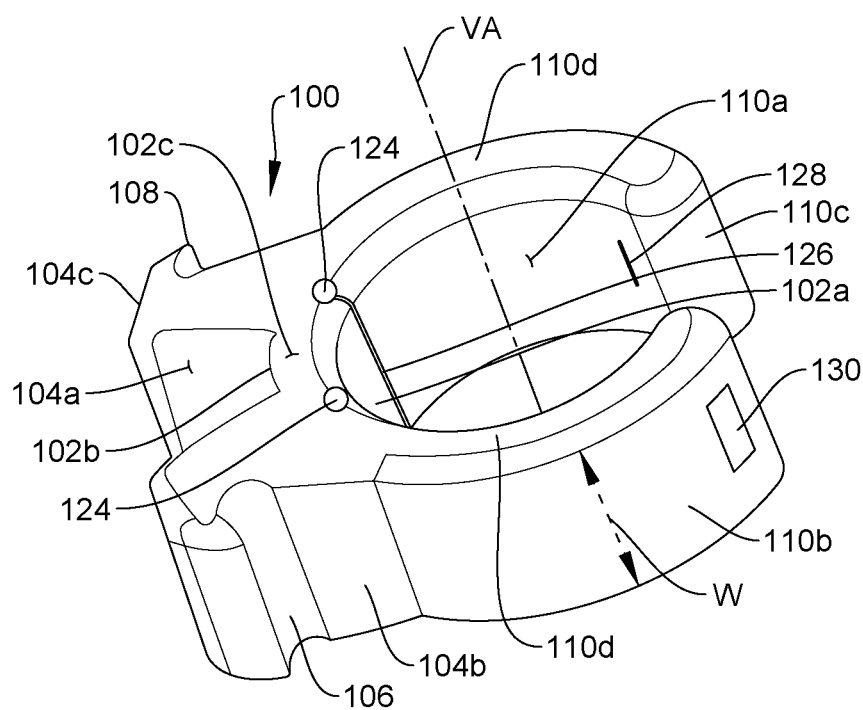
FIGS. 4A-B are top and bottom perspective views of a first embodiment of a body of an electrode cuff.
Figure 4B:
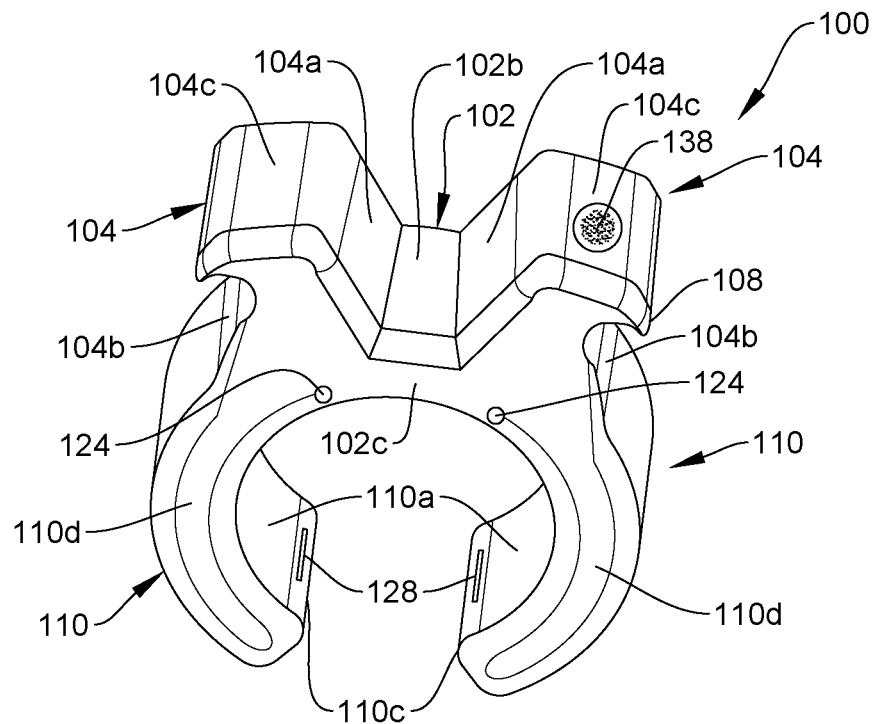
Figure 5A:
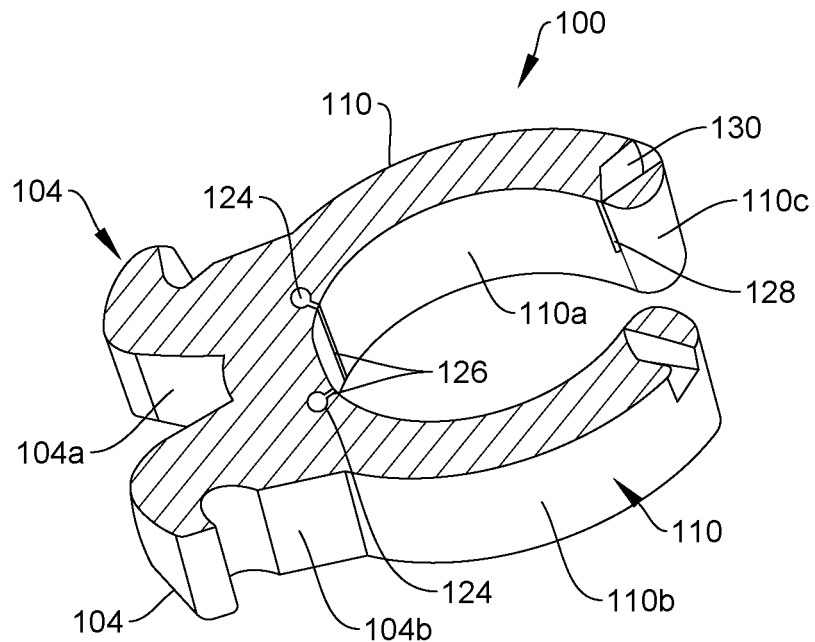
FIGS. 5A-B are perspective and plan cross-sectional views of the body of the electrode cuff, respectively.
Figure 5B:
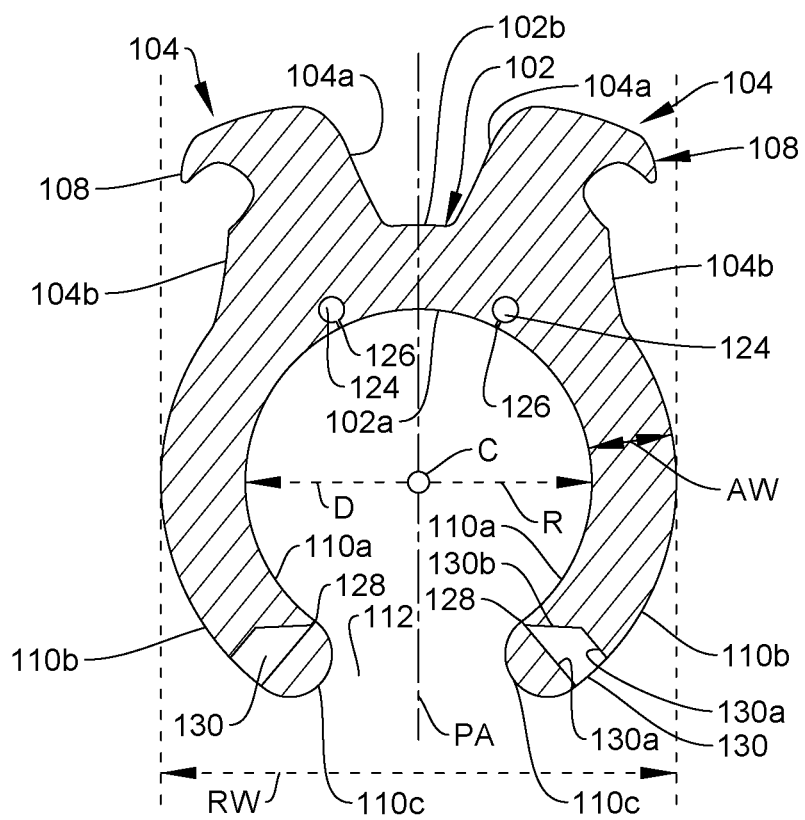

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what is presently believed to be the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

As used herein, "axial" means in the direction of an axis of a circular or annular object; "radial" refers to the direction along a radius or diameter of a circular or annular object; "annular width" refers to the width of a wall between an inner and outer radius of a circular or annular object; "about" with reference to a number means +/−10% of the number.

To provide for substantially continuous monitoring of, in particular, lumbar nerve roots during a spinal surgical procedure, I have developed an electrode assembly 100 having at least one electrode. The electrode assembly is configured to be positioned such that the electrode is in electrical communication with the lumbar nerve root. Further, the electrode assembly is sized and shaped such that it can remain in position during a spinal surgical procedure, to then be removed when the procedure is completed. With an electrode in contact with the lumbar nerve root, the surgeon can have substantially continuous monitoring throughout the surgical procedure. A single electrode will allow for either stimulation or recording at the lumbar nerve root. However, preferably, the electrode assembly comprises at least two electrodes which are positioned such that, when the electrode assembly is placed on the nerve root, the electrodes are circumferentially spaced from each other. As described below, with two electrodes in continuous contact with the nerve root, the surgeon can both stimulate and record at the lumbar nerve root.

In a preferred embodiment, the electrode assembly is in the form of a nerve cuff 100 which is shown FIGS. 4A-9. FIGS. 4A-5B show the body of the nerve cuff 100 and FIGS. 6-9 show the interior of the nerve cuff body. As will be described below, the nerve cuff 100 is sized such that it can be placed on the lumbar nerve root such that the electrode(s) of the nerve cuff remain in contact with the lumbar nerve root throughout a surgical procedure. The nerve cuff is then removed from the lumbar root upon completion of the surgical procedure.

Figure 13A:
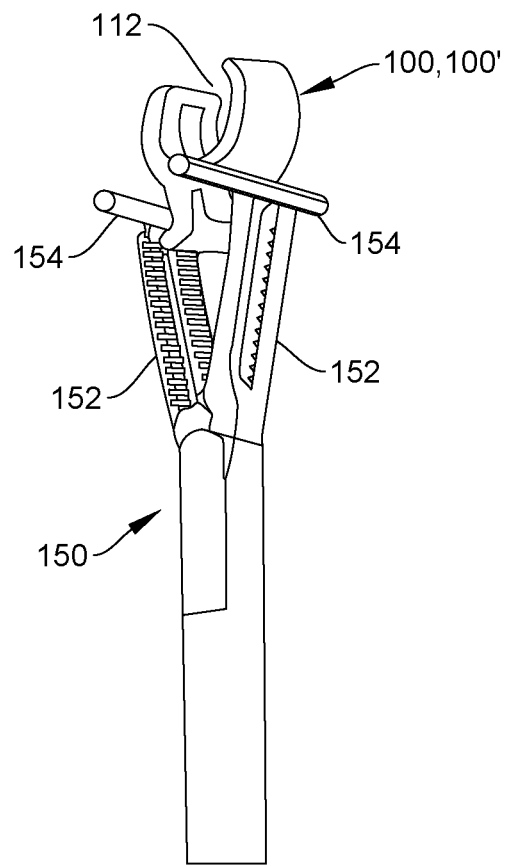
FIGS. 13A-B are perspective views of the electrode cuff being held by a modified laparoscopic grasper in partially and fully open positions, respectively.
Figure 13B:
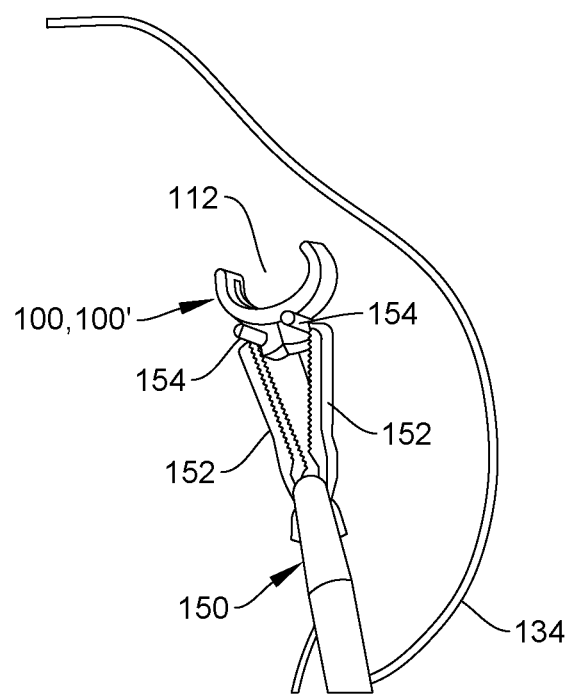

Turning to FIGS. 4A-5B, the nerve cuff 100 comprises a body comprising a base portion 102 having an inner curved surface 102a, an outer surface 102b, and opposed side surfaces 102c. A pair of grasping arms, grips, or ears 104 exend from the back surface 102b. Each ear 104 has an inner surface 104a, an outer surface 104b, and a back surface 104c. The base or root of the inner surfaces 104a of the grasping arms are spaced from each other, such that the two grasping arms are distinct and spaced apart. As seen, the inner surfaces 104a of the grasping arms diverge from each other. The outer surfaces 104b, as seen, are sloped or canted relative to an axis PA (FIG. 5B) of the nerve cuff which lies in a plane generally parallel to the side surfaces 102c of the base 102. An arcuate cutout 106 is formed on the outer surface 104b near the top of the each grasping arm. Finally, the end surface 104c extends over the cutout 106 to form a hook-like structure 108 at the top of the cutout. As will be described below, the cutouts 106 allow for a grasping tool, such as a modified laparscopic grasping tool, to grasp the nerve cuff, as seen in FIGS. 13A-B. The configuration and angle of the grasping arms 104 is exemplary only. It will be appreciated that the grasping arms 104 could have different configurations, profiles, angles, etc. as long as they can be gripped by the grasping tool to be opened, as described below, to be placed about a nerve root.

A pair of arms 110 extend from opposite sides of the base 102, with fixed ends of the arms extending from below the outer surfaces 104b of the grasping arms 104. The arms 110 each have an inner surface 110a, an outer surface 110b, an end surface 110c, and opposed side surfaces 110d. The outer surfaces 110b are illustratively shown to be curved (and to define a radius). However, the outer surfaces could have any desired shape. The outer surfaces 110b of the arms define a widest radial width RW of the nerve cuff 100 (as shown by dashed lines in FIG. 5B). The grips/ears 104 are sized, relative to the nerve cuff arms 110 such that the overall distance between the outer surraces 104b of the grips/ears is less than, or equal to (i.e., preferably no larger than) the largest radial width RW defined by the outer surfaces of the nerve cuff arms 110. That is, as illustratively shown in FIG. 5B, the grips/ears 104 do not extend beyond lines tangential to the outer surfaces of the arms 110 at their widest radial point. With the distance between outer surfaces of the grips/ears being less than, or equal to, greatest the side-to-side width of the nerve cuff arms, the grips/ears will not interfere with the surgical site, as can the ears/grips disclosed, for example, in U.S. Pat. No. 10,729,342.

The inner surfaces 110a of the arms 110 are arcuate, and as seen, continue the arc of the base inner surface 102a, such that the base inner surface 102a and the inner surfaces of the arms 110a define a single continuous arcuate surface having a radius R (FIGS. 5B, 7) extending from a center C which lays on a vertical axis VA (FIG. 4A) which is perpendicular to, and intersects, the planar axis PA. The arc defined by the combined inner surfaces 102a, 110a is at least 270°, preferably at least 300°, and more preferably about 306° (giving the nerve cuff 100 a cerclage of at least 75%, preferably at least about 83%, and preferably about 85%), such that the end surfaces 104c of the two arms are directed towards or generally face the planar axis PA. As can be seen, the nerve cuff is generally cylindrical. The arms have an axial width W (FIG. 4A) in the direction of the vertical axis VA of about 2-5 mm and an annular width AW (FIG. 5B) of about 1-3 mm, and preferably about 2 mm. The inner diameter D of the nerve cuff is sized such that when the nerve cuff is positioned about a nerve root, the inner sufaces 102a, 110a of the nerve cuff will be sufficiently close to the nerve (and preferably in contact with the nerve) such that electrical signals can be transmitted to, and received from, the nerve. That is, the nerve cuff will be in electrical communication with the nerve. For example, the diameter D of the nerve cuff can be about 2-10 mm, preferably about 2-8 mm, and more preferably about 4 mm, to define a diameter which is slightly larger than the diameter of the nerve root 12.

Figure 7:
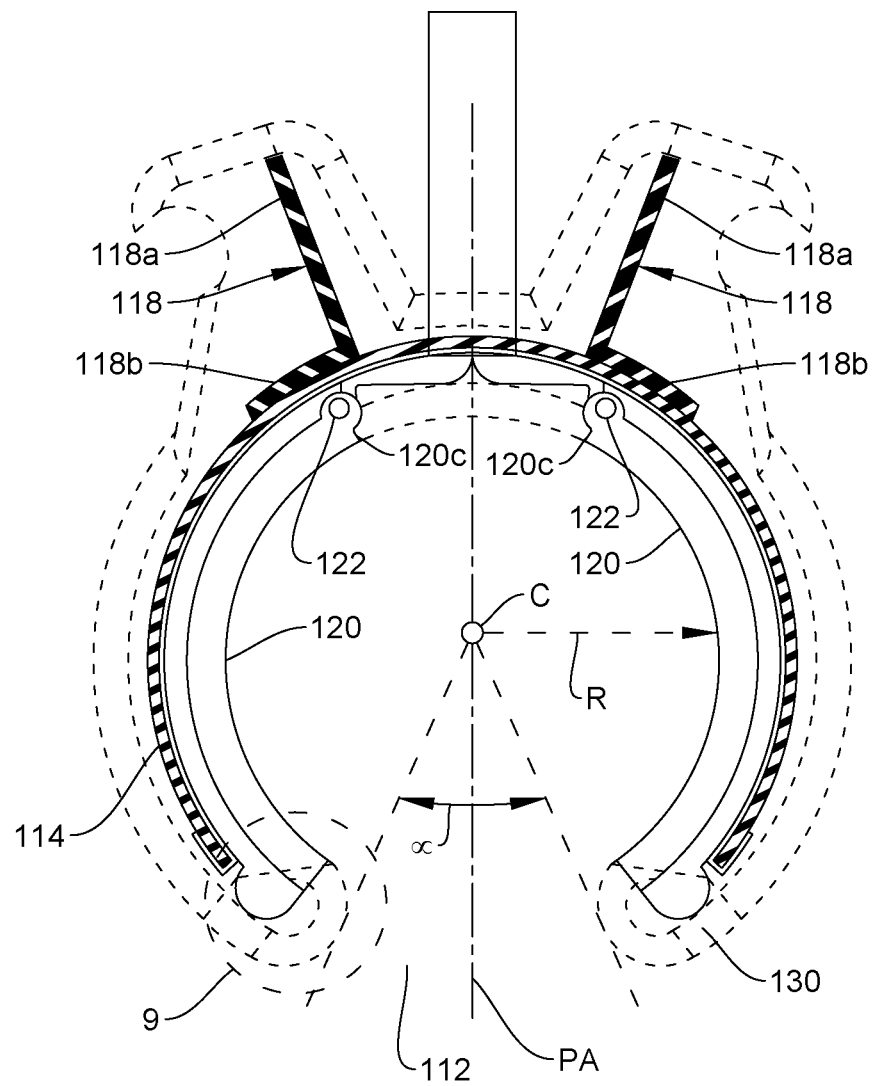
FIG. 7 is a horizontal cross-sectional view of the electrode cuff, again with the nerve cuff body shown in phantom.
Figure 9:
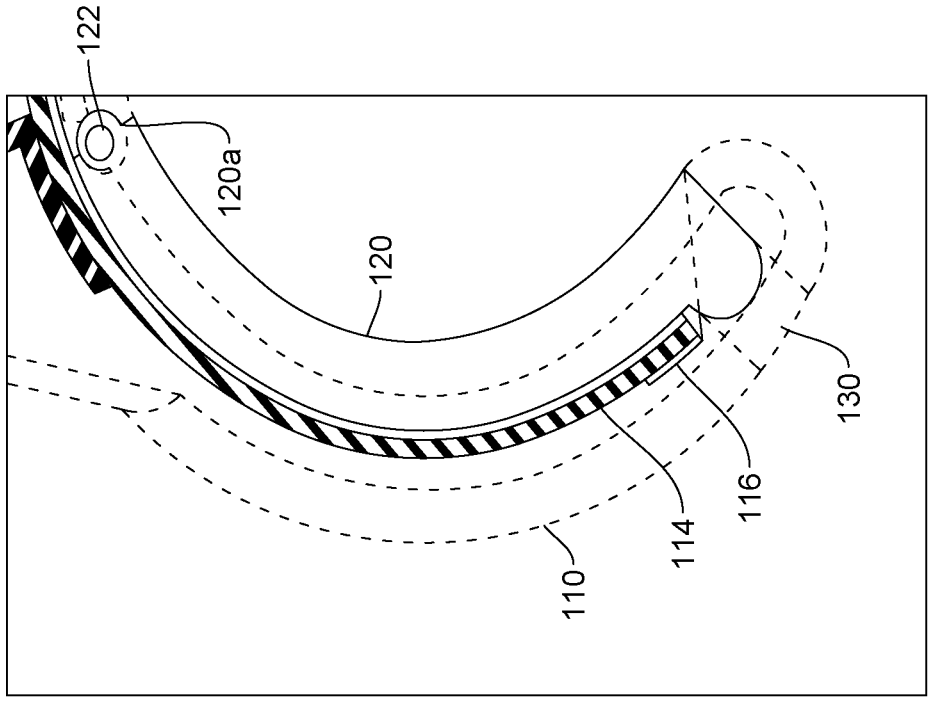
FIGS. 8 and 9 are enlarged sectional views taken along the circles 8 and 9 of FIGS. 6 and 7, respectively.
Figure 8:
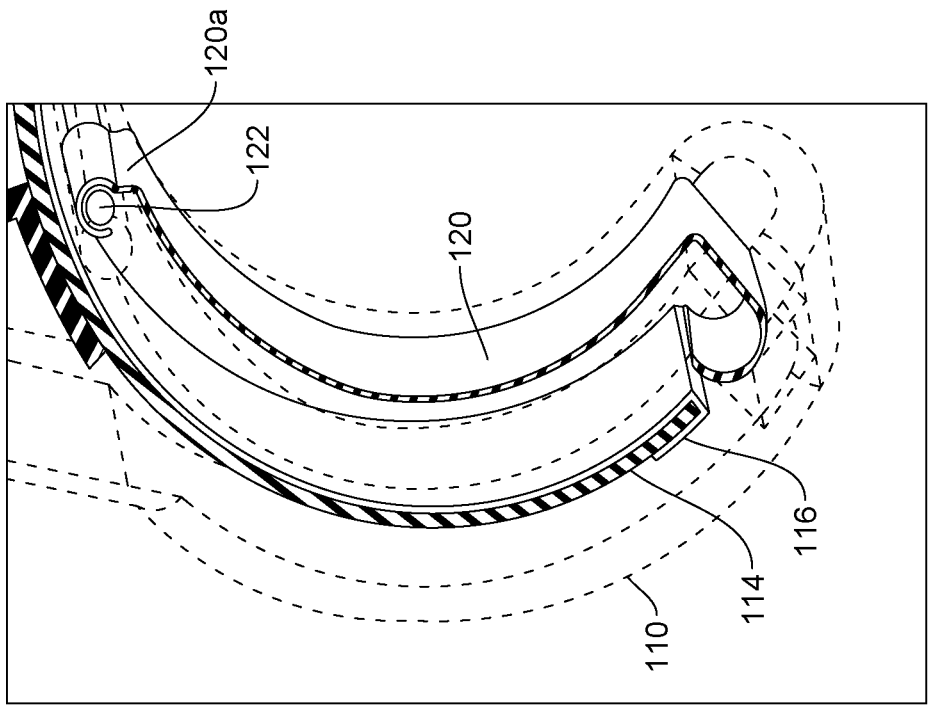

The ends 110c of the arms 110 are spaced from each other to define a gap 112 between the ends of the arms. Thus, as shown in FIG. 7, lines extending from the center C of the circle defined by the inner surfaces of the nerve cuff tangentially to the ends 110c of the arms define an angle a of less than 90°, preferably less than 60°, and preferably about 54°. Lastly, as seen, the ends of the arms are radiused, to avoid any sharp corners between the inner and outer surfaces of the nerve cuff 100.

The nerve cuff is formed from a material, and the arms 110 are sized and shaped, such that the arms are flexible and springy. Hence, the annular width AW of the arms is preferably constant, and thus the outer surfaces 110b of the arms are preferably arced as well, such that the inner and outer surfaces are generally concentric. The arms can flex between an at rest or relaxed position (FIG. 13A) wherein the gap 112 is narrowest and an open position (FIG. 13B) in which the gap is increased to a size sufficient to pass over a spinal nerve, such as the lumbar nerve root. In the relaxed position, the gap 112 between the ends 110c of the arms 110 has a width less than the diameter of the root of the spinal nerve, and in the open position the gap has a width that is greater than the diameter of the root of the spinal nerve. The spring-like quality of the arms enables the arms to spring back from the open position to the relaxed position when released. Thus, in the open position, the nerve cuff can be applied over the nerve root, and when released, the nerve cuff will return to its relaxed state in which it substantially surrounds or encircles the nerve root. As can be appreciated, when the nerve cuff 100 is moved between its relaxed and open positions, the nerve cuff will pivot about the upper surface 102b of the base. That is, when the nerve cuff is moved to the open position, the upper surface 102b of the base 102 will flex from a concave arc to a more flattened surface. The upper surface 102b of the base between the ears 104 thus defines a bending point or hinge portion of the nerve cuff. Preferably, the nerve cuff 100 is sized to encircle at least 75%, and preferably at least about 85%, of the nerve root. If desired, the nerve cuff can be sized to encircle 100% of the nerve root. As noted below, the size of the gap 112 in conjunction with the spring quality of the nerve cuff arms enables a nerve root surrounded by the nerve cuff to pop out of the nerve cuff 100 through the gap 112 without damaging the nerve if the nerve cuff is suddenly dislodged.

To facilitate the spring-like quality of the nerve cuff 100, at least the arms 110 are formed from a flexible material, such as 80 durometer silicone. For ease of manufacture, the entire cuff can be molded from this material. Additionally, the arms 110, as noted, have an annular width AW of about 1-3 mm and, preferably, of about 2 mm. This annular width enables the arms to be flexible. The arms can be narrower if desired. However, if the annular width of the arms is much greater than 3 mm, the arms become too stiff, and will lose their spring-like quality. Additionally, if the largest radial or side-to-side width RW of the nerve cuff substantially exceeds 12 mm, the nerve cuff will become too large for use in the limited space of the surgical site.

To further facilitate the spring-like quality, the nerve cuff 100 has a main spring 114 (FIGS. 6-9), preferably in the form of a leaf spring, which extends through the arms 110 and the base portion 102 of the nerve cuff. As can be appreciated, the main spring 114 facilitates returning of the nerve cuff to the relaxed position from the open position upon release. Preferably, the main spring 114 is a single continuous leaf spring which is generally centered between inner and outer surfaces of the arms 110. Additionally, as seen, the main spring 114 defines an arc that is concentric with the arc defined by the inner surfaces 102a, 110a of the base portion 102 and arms 110, respectively. The opposite ends of the spring 114 are preferably spaced inwardly from the ends 110c of the arms 110. In an alternative, the main 114 could comprise two spring portions, there being a spring extending through each arm. In this variation there would be no main spring element passing through the base portion 102 of the nerve cuff. Finally, the spring 114 is provided with an electrical insulating layer 116 that extends along the entire inner surface of the spring 114 and wraps around the ends 114a of the spring. The insulating layer can, for example, extend up to about 4 mm along the outer surface of the spring 114. The electrically insulating layer 116 is preferably formed from a polymer, such as a polyimide.

An L-shaped grip spring 118 extends from the main spring 114 into each gasping arm 104. The grip spring 118 includes an arm portion 118a and a foot portion 118b. The arm portion 118a extends from the main spring 114 into the gasping arm 104, at a position that is preferably closer to the inner surface 104a than to the outer surface 104b of the gasping arm. The foot portion 118b forms an angle (preferably of about 90°) with the arm portion and extends from a base of the arm portion a short distance along the main spring 114 in a direction towards the ends of the arms 110. That is, the foot portions 118b of the two L-shaped springs do not extend toward each other, but rather extend away from each other. The foot portions 118b are fixed to the main spring 114 by any desirable means, such as by welding, gluing, riveting, etc. Alternatively, the spring foot portions 118b can be held against the main spring 114 simply by the material of the nerve cuff which is molded about the springs 114 and 118.

Figure 6:
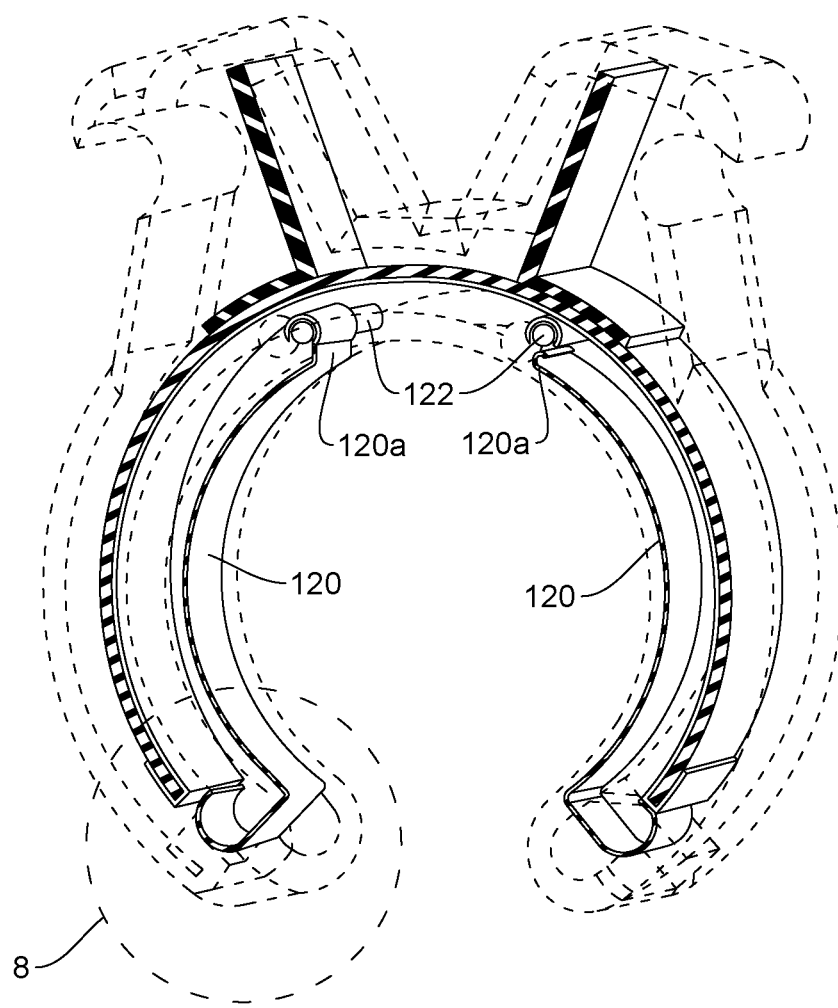
FIG. 6 is a perspective view of the body of the electrode cuff shown in phantom to show the electrodes and interior components of the electrode cuff.

The main spring 114 and the grip spring 118 are both formed from leaf spring material and are of generally equal axial width (in the direction of the vertical axis VA), as seen in FIG. 6. The main spring 114 can have an annular width or thickness of about 0.1-0.5 mm and an axial width of about 1-3 mm. In a preferred embodiment, the spring can, for example, be formed from nitinol and have an annular width or thickness of about 7mils (about 0.2 mm). Even with the spring 114, the nerve cuff remains sufficiently flexible such that a nerve surrounded by the nerve cuff can pop out of the nerve cuff 100 through the gap 112 without damaging the nerve if the nerve cuff is suddenly dislodged. If desired, the grip springs 118 can be omitted. In this case, the spring-quality of the arms 110 and the main spring 114 would be relied upon to return the arms to the relaxed position from the open position. Further, if the arms 110 are themselves sufficiently springy, the main spring 114 can be omitted. In another alternative, both the main spring 114 and the grip spring 118 can be omitted. This version, too, would rely on the inherent springiness of the nerve cuff to return the nerve cuff to the released position from the open position.

The body of the nerve cuff 100 can be formed, for example, by injection molding. The main spring 114 with its insulating layer 116 and the grip spring 118 can be positioned in the mold, such that the springs 114, 118 and insulating layer 116 are molded into place.

Figures 10A, 10B:
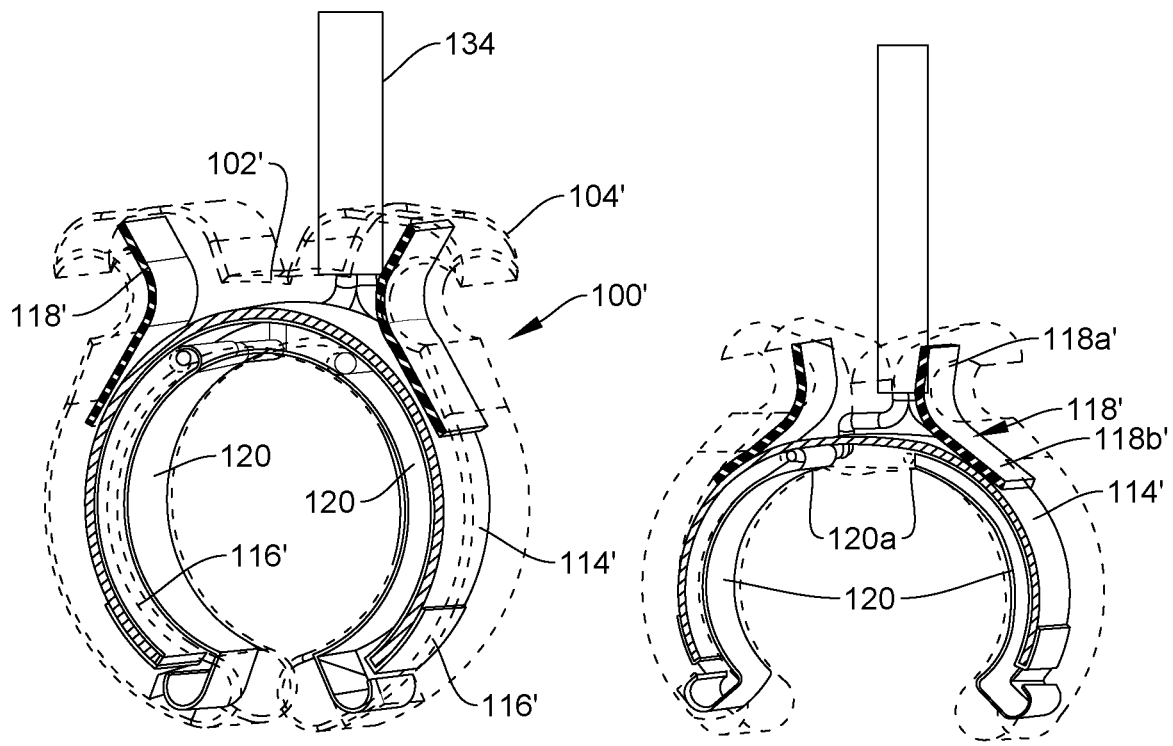
FIGS. 10A-B are perspective views of the slim line electrode cuff embodiment with the body in phantom, so that its interior components can be seen, with the electrode cuff in a relaxed state (FIG. 10A) and in an opened state (FIG. 10B)

FIGS. 10A, B and 11 show an alternative cuff 100'. The nerve cuff 100' is formed generally similarly to the nerve cuff 100, however, it is smaller than the nerve cuff 100. As shown in the comparison view of FIG. 11, the nerve cuff 100' has a smaller radial width than the nerve cuff 100, and a smaller axial width than the nerve cuff 100. The annular width of the arms 110 of the nerve cuff 100 are equivalent to the annular width of the arms 110' of the nerve cuff 100'. A comparison of some preferred dimensions are shown in the table below.

| Dimension | Cuff 100 | Cuff 100' |
|---|---|---|
| Radial Width (RW) | ~6-12 mm | ~5-8 mm |
| Axial Width (W) | ~2-5 mm, preferably ~5 mm | ~3 mm |
| Annular Width (AW) | ~1-3 mm, preferably ~2 mm | ~1-3 mm, preferably ~2 mm |
| Inner Diameter (D) | ~2-10 mm, preferably ~4 mm | ~3-6 mm |
| Cerclage | ≥75%, ≥83, ≥85% | ≥90% |

Figure 11:
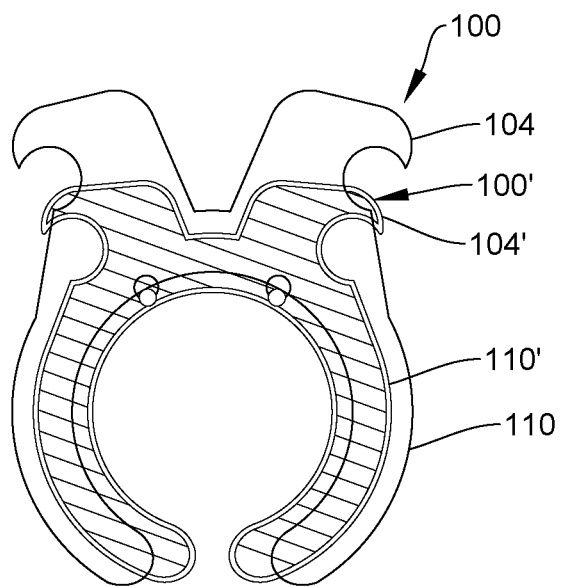
FIG. 11 is a plan view comparing slim line electrode cuff embodiment of FIGS. 10A-B to the electrode cuff of FIGS. 4A-D.

In addition, as seen in the comparison view of FIG. 11, the inner surface of the base and arms 110' of the nerve cuff 100' defines a greater arc than does the inner surface of the nerve cuff 100. Where the nerve cuff 100 defines a cerclage of preferably about 85%, the nerve cuff 100' defines a cerclage of about 90% or more. Thus, the arc defined by the inner surface of the base and arms of the nerve cuff 100' is at least about 325°. Additionally, as seen, the grasping arms 104' are of a lower profile than the grasping arms 104 of the nerve cuff 100. That is, the grasping arms 104' do not extend from the base 102' of the nerve cuff 100' as far as the grasping arms 104 of the nerve cuff 100. This smaller size of the grasping arms allows for the nerve cuff 100' to be used in conjunction with smaller nerve roots and allow use for a smaller surgical site.

Like the nerve cuff 100, the nerve cuff 100' internally, includes a main spring 114' and a grip spring 118'. Like the nerve cuff 100, the inner surface of the main spring 114' is covered with an insulating layer 116' which wraps around the end of the main spring 114' and extends along a portion of the outer surface of the main spring 114'. Due to the smaller size of the nerve cuff 100' and its grasping arms 104', the grip spring 118' is formed slightly differently than the grip spring 118. The arm portion 118a' is shorter than the arm portion 118a, and the leg portion 118b' extends over a larger extent of the main spring 114' than does the leg portion 118b of the grip spring 118. Further, the arm and leg portions 118a',b' define a bigger angle than the arm and leg portions 118a,b of the grip spring 118, such that the junction between the arm 118a' and leg 118b' of the grip spring 118' defines more of a gradual bend. This bent configuration of the grip spring 118' allows for a larger leg portion 118b' which, in turn, will generate a greater arm moment when the nerve cuff is moved from a relaxed to an open position (described below) for application of the nerve cuff to a nerve. This bent configuration of the spring also minimizes the potential for the grip spring of being truly vertical (i.e., the arm portion being parallel to the planar axis PA) when activated with a grasper to help prevent the nerve cuff from popping off of the grasper during placement. The lower profile ears 104' meet in the middle during opening as seen generally in FIG. 10B, thereby preventing over-opening which could damage internal spring 114'.

In accordance with one embodiment, the nerve cuff 100, 110' is a bipolar electrode cuff, and to this end has two discrete electrodes 120, there being at least one electrode on each arm. FIGS. 6-10B illustratively show the nerve cuff 100, 100' with one electrode 120 on each arm. The electrodes 120 are formed from an electrically conductive ribbon or foil, formed, for example, from platinum, which extends along the inner surface 110a of each arm. Each ribbon/foil is connected at an inner end 120a (FIG. 8) to an electrically conductive post 122 which is lodged in place in the base portion 102 beneath each grasping arm 104. The posts 122 can, for example, be received in holes 124 in the base portion 102 of the nerve cuff. A slot 126 (FIG. 4A) extends from the base portion inner surface 102a to each hole 124, such that the ribbon/foil 120 can extend from the post 122 through the slot 126 to the inner surfaces 102a, 110a of the nerve cuff. The ribbon/foil extends smoothly along the inner surfaces 102a, 110a of the nerve cuff with the opposite end 120b of each ribbon/foil passing through a second slit 128 in the inner surface 110a of each arm proximate the ends 110c of the arms 110 to be secured in a chamber 130 that opens to the outer surface 110b of each arm. The chamber 130 has opposed side walls 130a joined by a sloping inner wall 130b. As seen in FIG. 7, the ribbon/foil is illustratively shown as having a hook shape in the chamber 130. Although the chamber is shown as having a sloping inner wall 130b, the inner wall could, instead be domed to accommodate the hook shape of the ribbon/foil. This would provide a greater gluing surface for the ribbon/within the chamber 130. As shown, each ribbon electrode defines an arc from the first slot 126 adjacent the post 122 to the second slot 128 proximate the end 110c of the arm of about 120°-140°, preferably about 125°-135°, and most preferably, of about 130°. The foil ribbons 120 have an axial width (in the direction of the vertical axis VA) of about 1-3 mm, and preferably about 2 mm which is less than or equal to the axial width of the arms. The slots 126 and 128 are sized to receive the foil electrodes 120, and thus have axial lengths of slightly greater than the axial width of the foil electrodes. In fact, the electrodes 120 of the nerve cuff 100' have an axial width that is generally equal to the axial width of the electrode foils of the nerve cuff 100, and thus have an axial width of about 2 mm.

Figure 12:
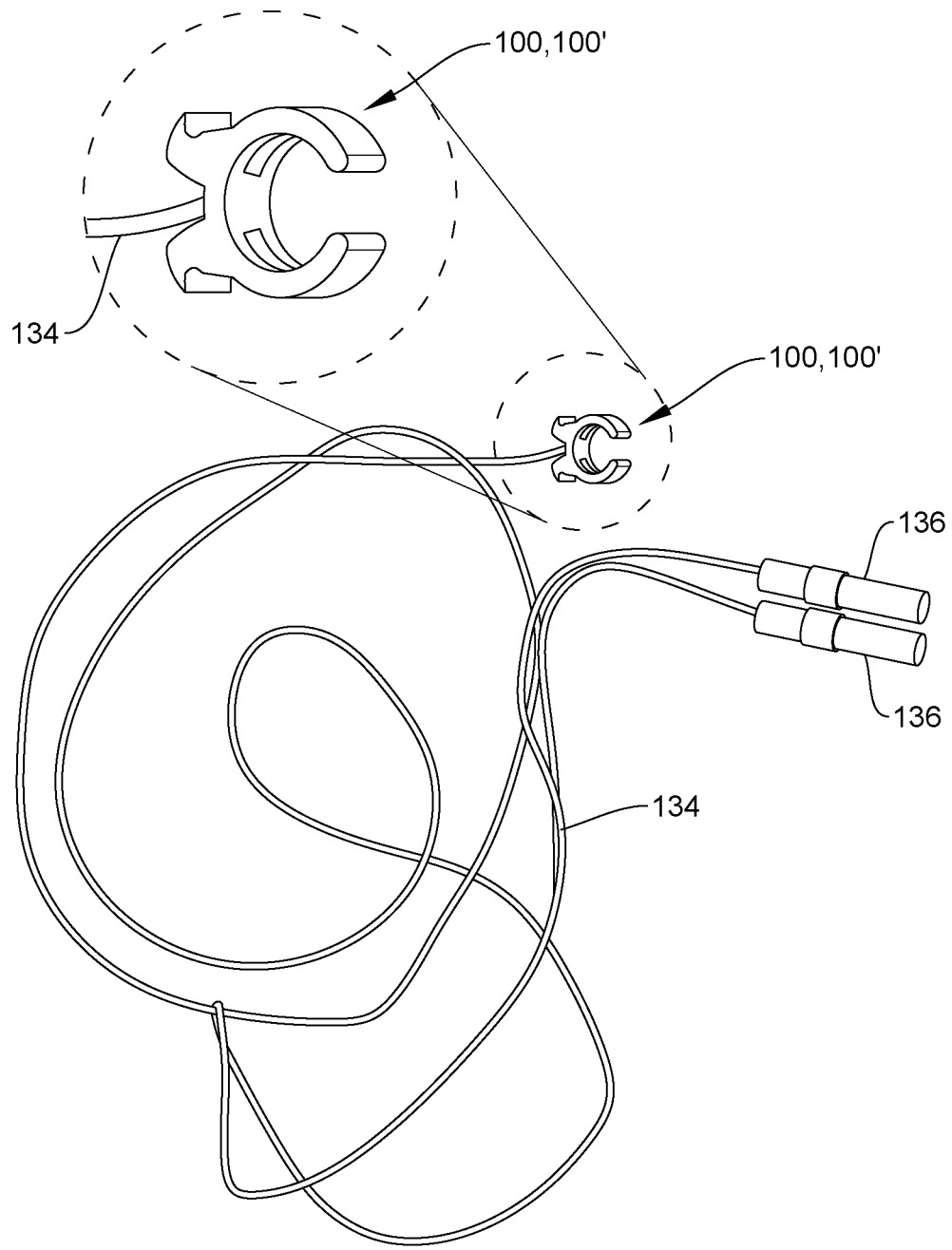
FIG. 12 is a perspective view of an electrode cuff with an electrical cord extending from the nerve cuff and having connectors at the end of the cord, with an enlarged view of the electrode cuff.
Figure 14:
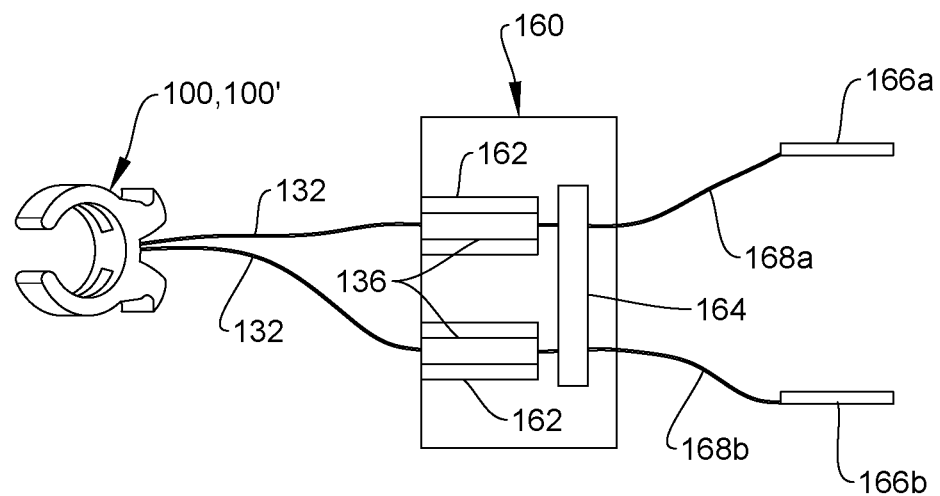
FIG. 14 is a schematic drawing of the electrode cuff connected to a monitoring device with leads extending between the nerve cuff and the monitoring device.

The two posts 122 are electrically connected to independent wires 132 (FIG. 14) which are encased in a single cable 134 (FIGS. 10A and 12) which, as shown, extends from the base 102 between the grasping arms 104. The two wires 132 are electrically insulated from each other, and at their far ends, are provided with connectors 136 (FIG. 12) which enable the wires to be electrically connected to a stimulating/monitoring device 160 (FIG. 14). The two posts 122 are spaced apart from each other a distance sufficient to avoid leakage or signals from one pin being received by the other. For example, the two pins 122 can be spaced apart about 2-6 mm depending on the size of the nerve cuff. As is known, the connectors 136 can be color coded to facilitate proper connection of the nerve cuff to a monitoring device 160. For example, often, one of the connectors is white and the other is blue. The nerve cuff 100, 100' can be provided with indicia to enable the technician to know which electrode foil 120 is electrically connected to which plug 136. Thus, for example, the nerve cuff 100 can be provided with a colored area 138 (FIG. 4B) on at least one of the grasping ears 104 which corresponds to, or is indicative of, the connector 136 to which the particular electrode is electrically connected. For example, a blue strip or dot can be formed on the ear which is effectively above the electrode 120 which is connected to the blue connector 136. This indicia could also (or alternatively) be placed on the arm.

The foils of the electrodes 120 are preferably anchored only at their ends, and thus are anchored only to the posts 122 at the wire interface and in the chambers 130 at the ends of the nerve cuff arms. The posts 122 to which the wires 132 are connected are installed in the holes 124 in the nerve cuff base. One end of the electrode foil is threaded through the slot 126 to be connected to the post 122, and the other end of the electrode ribbon/foil 120 is threaded through the slot 128 near the ends 110c of the nerve cuff arms 110. To mount the ribbon/foil 120 to the nerve cuff, the nerve cuff can be clamped on a mandrel of the size of the nerve cuff ID. While on the mandrel an end of the ribbon/foil is folded over in the chamber 130 and the chamber 130 filled with silicone adhesive. Silicone adhesive is also applied in the post holes 124 to insulate the wire 132 and the electrode ribbon/foil soldered to the post 122. Securing of the electrode ribbon/foil is accomplished with the nerve cuff on the mandrel to shape the ribbon/foil. In this procedure, adhesive is not used along the inner surfaces 110a of the nerve cuff arms 110. Thus, when the nerve cuff is fully opened the electrode ribbon/foil may pull away slightly from the inner surfaces 110a of the arms until released on the nerve where it will return to the formed (curved) shape. This is believed to provide a strain relief on the electrode ribbon/foil and electrode foil/post/wire interface. The mechanical anchoring in the silicone in the hole 124 and the chamber 130 is thus the main means of securing the electrode foil in place the nerve cuff. In an alternative, the electrode ribbon/foil could be glued or otherwise adhered to the inner surface of the nerve cuff base and arm using an appropriate adhesive or tacking.

As noted, there is an electrically insulative layer 116 on the inner surface of the main spring 114 and which extends around end 114a of the main spring 114 to cover a short distance of the outer surface of the main spring 114. This insulating layer 116 is thus positioned between the main spring 114 and the ribbon/foil electrodes 120 at all points of the ribbon/foil electrode. Due to the annular width of the arms 110, the physical distance between the ribbon/foil electrodes and the spring many only be about 1-2 mm. Although the material from which the nerve cuff is made is non-conductive, due to the thinness of the arms 110, electrical impulses could pass from the ribbon/foil electrodes 120 to the main spring 114. The electrically insulating layer 116 thus reduces, or even eliminates, the potential for electrical impulses to pass between the ribbon/foil electrodes and the main spring 114, and thereby reduces the potential for the spring to interfere with the monitoring function provided by the nerve cuff. To better ensure electrical isolation of the ribbon/foil electrodes from the spring, the insulating layer is preferably wider than the main spring (in the direction of the vertical axis VA). Thus, for example, the main spring 114 can have an axial width of about 2 mm and the insulating layer 116 can have an axial width of about 3 mm.

Although the construction of the electrodes and the manner of securing the electrodes is described with respect to the nerve cuff 100, it will be understood that the electrodes 120 of the nerve cuff 100' are secured in the same manner.

Figure 15:
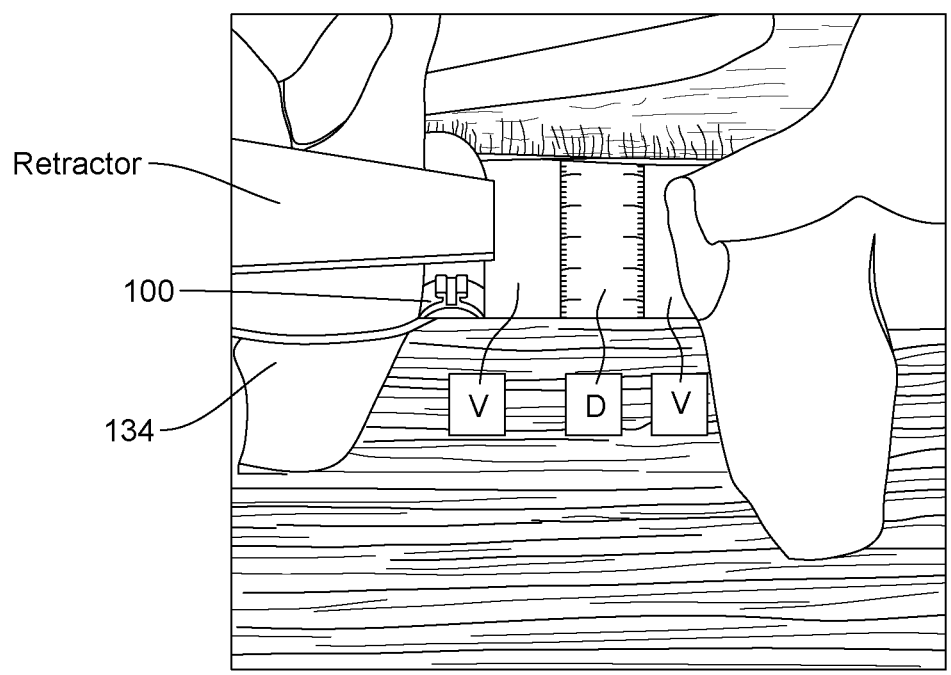
FIG. 15 is a schematic drawing showing the electrode cuff positioned about an exiting lumbar spine nerve root in a surgical procedure.

In use, the nerve cuff 100, 100' is applied around the root of a nerve proximate the spine, as shown illustratively in FIG. 15. The nerve cuff is sized to be applied to the root of the lumbar nerve, but could be sized to be applied to any of the spinal nerves. As shown in FIGS. 13A-B, to place the nerve cuff on the nerve, the nerve cuff 100, 100' is held by a modified laparscopic grasping tool 150 having arms 152 with bars 154 at the ends thereof. The bars 154 are sized to be received in the grasping cutouts 106 of the grasping arms 104 of the nerve cuff. As can be appreicated, the bars 154 are sized such that they can be received in the cutouts 106 of the grasping arms 104 in such a manner that the nerve cuff will be securely held by the grasping tool 150, but whereby the bars 154 can be easily withdrawn from the cutouts when the nerve cuff is released from the grasping tool. Once grasped, the grasping tool 150 is operated to open the nerve cuff 100, as seen in FIG. 13B. The nerve cuff is then positioned around the lumbar nerve root, as seen in FIG. 15 and released. The nerve cuff 100 can be positioned lateral to the retractor blade as shown in FIG. 15. Alternatively, the nerve cuff can be placed behind the retractor blade in a protected position if placing cuff lateral of the retractor blade encroaches on a surgical corridor. With the nerve cuff in position, opposed ribbon/foil electrodes 120 will be on opposite side sides of the nerve with each ribbon/foil electrode 120 being proximate, or in contact with, the nerve root about a substantial portion of the nerve root to be in electrical communication with the nerve root. That is, the use of ribbon/foil electrodes provides for a greater contact area, and thus better electrical communication, with the nerve root; and the two ribbon/foil electrodes 120, in combination, are proximate or in contact with and will encircle the nerve root about a substantial portion of the circumference of the nerve root. The two ribbon/foil electrodes and the gap between the slots 126 in the nerve cuff base inner surface 102a in combination encircle about 80%-90%, and preferably about 85%, of the nerve root. The nerve cuff 100', with its greater cerclage, may encircle a greater amount of the nerve, and thus may encircle about 90%-95% of the nerve. This greater cerclage may decrease risk of cuff dislodging from nerve. Additionally, as noted, the two ribbon/foil electrodes will surround the nerve at, preferably, the same axial position along the nerve; that is, the two electrodes are not longitudinally/axially spaced along the nerve, but are circumferentially spaced about the nerve. As noted below with respect to FIGS. 17A-B, some axial spacing can be beneficial. Finally, each ribbon/foil electrode 120 defines an arc of less than 180°, with the arc defined by each ribbon/foil electrode preferably being about 120°-140°. As noted above, at the nerve root 12, the motor and sensory bundles are separate from each other. Thus, the nerve cuff can be positioned on the nerve root with one ribbon electrode about the sensory nerve bundle and the other ribbon electrode about the motor nerve bundle. Further, because the electrodes are in the form of foil ribbons, the nerve cuff can be rotated about the nerve to align the ribbon electrodes with the nerve in a desired manner. This thus allows for the electrodes to be positioned over the motor and sensory nerve bundles, so that signals to and from the motor and sensory nerve bundles can be separately provided and monitored.

Turning to FIG. 14, to monitor the nerve, the electrodes for the nerve cuff 100, 100' are connected to a standard monitoring device 160 (which can generate a pulse signal) via its leads 132 and connectors 136 in well known manners. For example, the connectors 136 are separately received in ports 162 in the device 160 to connect the nerve cuff to appropriate monitoring circuitry 164 contained within the device 160. The monitoring device 160 further includes two electrodes 166a,b which are connected to the monitoring device and the circuitry 164 within the monitoring device via leads 168a,b. The electrodes 166a,b are needles or surface contact pads defining remote electrodes which are applied to the patient. For example, the remote electrode 166a,b can be located in or placed on the scalp, muscle, peripheral nerve, dorsal spine, or abdomen. It is understood that the remote electrodes 166a,b maybe present in a plurality of different configurations (as noted below) reflecting multiple remote electrode connectivities. Thus, when the nerve cuff 100, 100' is positioned about a nerve, the electrical network is defined by the nerve, the two ribbon/foil electrodes 120, and at least one of the remote electrodes 166a,b.

The unique structure of the nerve cuff, i.e., the two distinct ribbon/foil electrodes which can be oriented to contact different circumferential areas of the nerve root, provides for more and better options for monitoring of the nerve. Preferably, the nerve cuff is used in combination with at least one remote electrode (i.e., a scalp, muscle, peripheral nerve, or dorsal spine electrode) to define a monitoring paradigm. For example, the scalp electrode can be activated to simulate the brain, and then the signal could be recorded at the nerve cuff electrode. This brain (stimulate)-cuff (record) electrode network would define a new transcranial evoked nerve action potential (TcNAP) performed with the patient anesthetically paralyzed or relaxed while the surgeon maintains retraction on the nerve root of interest. Currently TcMEPs are recorded in the distal muscle with an intramuscular or subdermal needle electrode, mandating special anesthesia protocols, i.e., TIVA (total IV anesthesia) with no muscle relaxation. It should also be noted that cuff monitoring of an individual nerve root will always be more specific and sensitive to root injury than electromyography (EMG) that records responses derived from multiple nerve roots that innervate that particular muscle.

Figure 16A:
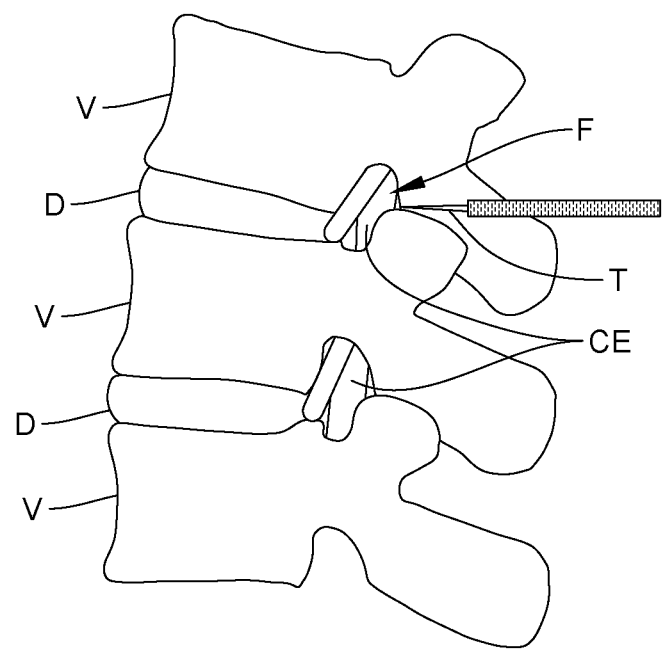
FIGS. 16A,B are schematic lateral and posterior/anterior (PA) views of a spinal column demonstrating placement of electrode needles for transforaminal stimulation of the proximal cauda equina.
Figure 16B:
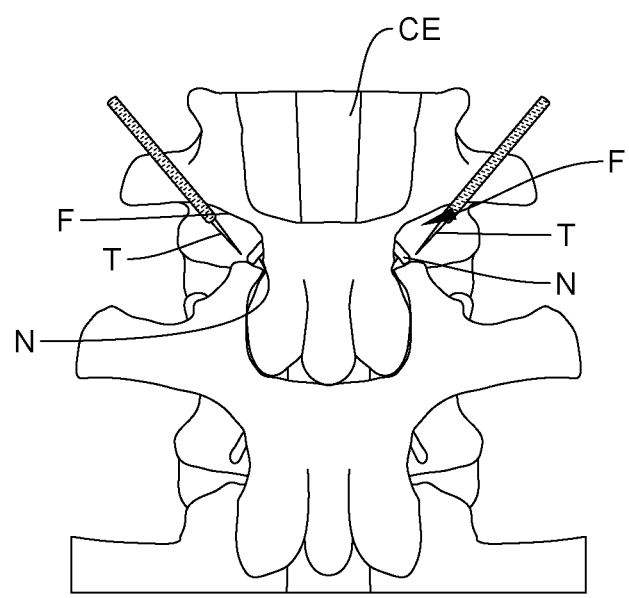

In addition to traditional TcMEP, an alternative site of stimulation utilizes the transabdominal TaMEP modality. In this instance, dorsal spine electrodes (cathodes), typically placed at T12-L1, are positioned on the patient's back to stimulate the cauda equina (CE) with an abdominal surface anode pad electrode being opposite the dorsal cathode electrode. Traditionally, responses are recorded distally in muscle via EMG. Dorsal spine electrodes are typically either a surface contact pad or subdermal needles. The remote cathode electrodes could be deep subfascial needles that are partially insulated. These deep subfascial needles would be electronically linked. Longer length and partially insulated needle electrodes are currently available for intramuscular use. However, when inserting needles paramidline subfascially, current would not be shunted by the integumentary system and superficial fat, as occurs when a surface contact pad or subdermal needle is used. Rather, current would be more efficiently directed across the spinal canal towards the abdominal anode pad, stimulating the cauda equina/nerves. Another version of dorsal spine stimulation would utilize transforaminal stimulation of the proximal cauda equina CE. Deep subfascial needle electrodes could be inserted T12-L1 bilaterally paramidline just lateral to the pars interarticularis to a depth of approximately the roof of the foramen. As shown schematically in FIGS. 16A-B, the tip T of the needle electrode would be approximate the dorsal roof of the intervertebral foramen F. Given separation of electrodes across the T12-L1 midline, the needle electrodes could be used in a quasi-bipolar configuration. Current would no longer have to travel significant transabdominal distances which require very large stimulus intensities, e.g., 450 mA. Rather, the relatively short distance of the quasi-bipolar configuration shown in FIGS. 16A,B would dramatically decrease stimulus intensity and eliminate the need for the abdominal anode pad. Finally, replacing EMG (electromyography) with neurogenic recording with the nerve cuff electrode would permit monitoring with the patient completely anesthetically relaxed or paralyzed.

Alternatively, the nerve cuff electrode can be activated to stimulate the spinal nerve, and then the signal could be recorded at the scalp (brain) electrode. This cuff (stimulate)-brain (record) electrode network would define a new somatosensory evoked potential (SSEP). Currently SSEP stimulate peripheral nerves such as median, ulnar, and posterior tibial nerves. This modality is used to assess spinal cord integrity and function, but not individual lumbar spinal nerve roots. This is because multiple nerve roots contribute to the origin of the peripheral nerves. Traditional SSEP would not be sensitive or specific to a particular nerve root. By stimulating an individual nerve root selectively as is possible with the nerve cuff 100, 100', SSEP could be used to monitor spinal cord and/or lumbar nerve roots.

As can be appreciated, the bipolar electrode cuff 100, 100' can be used with several different monitoring paradigms. Some of these paradigms include, for example:

1. brain (stimulate)-cuff (record)
2. dorsal spine (stimulate)-cuff (record)
3. peripheral nerve (stimulate)-cuff (record)
4. cuff (stimulate)-muscle (record)
5. cuff (stimulate)-brain (record)
6. cuff (stimulate)-dorsal spine (record).

Other paradigms can be envisioned.

In these paradigms, the recording and monitoring of the signals assume that the electrodes are in pairs, with one electrode being active, the other electrode being a reference or comparison electrode. The goal is to maximize signal to noise ratio (SNR) given that all recording electrodes can act as antenna. An operating room is a very challenging environment given all the electrical equipment-powered tools and devices, surgical cautery, lights, etc. All this equipment can generate signals that can affect the signal that is picked up by the nerve monitoring equipment. By getting the reference electrode as close as possible to the active electrode, the signal noise from other equipment in the operating room can be significantly limited. Further, with the nerve cuff 100, 100', either of the two electrodes can be made an active electrode, i.e., to record signals. The other electrode will then be an inactive electrode in which case the reference electrode will be remote, e.g., proximate a surgical wound, or easily identifiable local anatomic structures (e.g., iliac crest, mirror image anatomic site, etc.). Alternatively, by having a reference electrode in one arm of the nerve cuff and an active electrode in the other arm of the nerve cuff, the nerve cuff 100, 100' allows for a reference electrode to be physically very close to active electrode. This arrangement could maximize the signal to noise ratio (SNR).

The nerve cuff 100, 100' in the aforementioned monitoring paradigms also has bipolar stimulation functionality. One foil acts as the stimulating pole (generally cathode pole) or electrode and the other foil as the return pole (generally anode pole) or electrode for current. Because the two poles are so physically close, current does not spread to surrounding tissues. This feature is advantageous when using the nerve cuff in close proximity to lumbar plexus or other nerves in proximity to target nerve of interest.

Further discussion regarding the unique ability of the bipolar nerve cuff 100, 100' to operate with patient paralysis is enlightening. Patients are generally anesthetically relaxed or paralyzed for most surgeries. This is beneficial for a surgeon, as it is easier to retract muscle and expose anatomy with the muscle relaxed. Paralyzing the patient also avoids the need to "fight" contracted muscles when positioning retractors. However, if a patient is paralyzed, the muscles will not contract in response to stimulation which will make monitoring of the nerves difficult. In spinal surgery where nerve or spinal cord monitoring is desired, MEP (motor evoked potential) based monitoring techniques prohibit paralysis as EMG (electromyographic) responses in non-paralyzed muscles must be recorded, and EMG responses cannot be recorded if the patient is paralyzed. Exposure of target anatomy becomes more difficult for the surgeon when the patient is not paralyzed because the muscles are not relaxed. Additionally, TcMEP relies on a large stimulating charge, which can cause the patient's body to, at a minimum, move; but generally, the patient's body jumps, as neck, arm, abdominal, and leg muscles are indiscriminately stimulated and contract. Thus, the surgeon has to step back from the table when such a charge is applied to the patient. Additionally, a bite block must be used to prevent the patient from lacerating his/her tongue. However, the nerve cuff 100, 100' can be used with the patient paralyzed. Transcranial evoked NAP (nerve action potential) thus can be recorded in the nerve cuff 100, 100' without requiring the signal/stimulus to travel down the plexus, then to the peripheral nerve, then to a non-relaxed muscle to be recorded. Thus, the patient will not jump or move in response to the stimulus, and the surgeon does not need to interrupt his/her dissection or operation. Thus, the nerve cuff 100, 100' will allow for substantially continuous recording of the nerve for monitoring purposes, rather than intermittent transcranial or transabdominal stimulation and EMG monitoring. Here, "substantially continuous" means issuing a stimulating signal much more frequently than was otherwise possible. For example, at least once every five minutes, and preferably once every two minutes or once every minute or even more frequently (such as every thirty seconds). Other monitoring time periods are possible as well. This substantially continuous monitoring is made possible by the fact that the patient can be paralyzed during the surgical procedure and that the signal response (i.e., the NAP, or nerve action potential) can be read at the nerve cuff 100, 100'.

FIGS. 6-9 and 10A,B demonstrate the nerve cuff as a bipolar electrode cuff (i.e., with one electrode extending along the inner surface of each arm 110, 110' of the nerve cuff). Further, as seen, in FIGS. 6-9 and 10A,B, the electrodes 120 are seen to be colinear-that is, they are not axially offset from each other. FIGS. 17A-C show alternative electrode/foil configurations. FIG. 17A shows a bipolar cuff 100A with one electrode extending along substantially the full length of each arm (similarly to the nerve cuff electrodes described above). However, in the nerve cuff 100A, the two electrodes are spaced axially from each other (i.e., the two electrodes/foils are positioned in different axial planes). Thus, for example, one electrode is closer to a back surface of the nerve cuff and the other electrode is closer to a front surface of the nerve cuff. In this embodiment, the foil is narrower—it is about 1 mm, rather than about 2 mm, allowing for the foils to be axially shifted without increasing the axial width of the nerve cuff.

FIGS. 17B and 17C show a cuff 100B, 100C, respectively, wherein each arm of the nerve cuffs is provided with two discrete electrodes 120a-d, with electrodes 120a,b being on one arm and electrodes 120c,d being on the other arm. The electrodes 120a,b are electrically isolated from each other, as are the electrodes 120c,d. Each electrode 120a-d is thus provided with its own wire which leads to a connector which can them be received in a monitor (similar to the monitor 160). To this end, the nerve cuffs of FIGS. 17B,C would include pin holes for pins to which each electrode is electrically connected, with the wire for each electrode being connected to a respective pin. In FIG. 17B, the electrodes 120a,b are axially offset from the electrodes 120c,d (are positioned in different axial planes) and in FIG. 17C, the electrodes 120a-d are all axially aligned (i.e., are all in the same axial plane).

All recording relies on comparing signals in a pair of electrodes to optimize the signal and subtract out noise. As previously mentioned, this is accomplished using a reference electrode in combination with active recording electrode. It is assumed that noise will be in common in both the active and reference electrode, but signal will only be present in the active electrode. Hence when differentially compared, the noise is canceled, leaving the signal. Conversely, if active and reference electrode both see the desired signal, then the signal will completely cancel out. Finally, if active and reference electrode are physically close, phase differences can be relied upon. This allows for common noise to be completely canceled, but the desired signal which is out of phase is only partially canceled.

The nerve cuff 100A (FIG. 17A) has a bipolar design which can be used for bipolar recording. One electrode would be an active electrode and the other electrode would be a reference electrode. The active and reference electrode are shifted axially by about 1 mm. In the nerve cuff 100A, the electrodes are about 1 mm wide rather than about 2 mm, enabling the nerve cuff 100A to have an axial width of about 3 mm. In this embodiment, because of phase shift, there is a resultant small differential signal. The noise at both electrodes given close proximity (i.e., of about 1 mm) would be essentially the same and should substantially cancel out. Additional improvement in noise reduction could come with averaging, further defining the small differential recorded signal.

The nerve cuff 100C (FIG. 17C) uses 4 electrode focal contacts rather than the 2 hemifoils of cuff 100A (FIG. 17A). This geometry favors anatomic segregation of the nerve bundles, but is more precise. Minimal rotation of the nerve cuff would position one contact completely over the motor nerve bundle and another contact completely over the sensory nerve bundle in the nerve root. As noted, the nerve cuff 100C requires 4 separate wires. During surgery, the surgeon and tech can select pairs from the four electrodes and compare combinations to determine which pair provides optimal signal. Thus, for example, the reference/active electrode pair can be electrodes 120a,d or 120a,c or 120b,d or 120b,c.

The nerve cuff 100B (FIG. 17B) effectively combines the embodiments of cuffs 100A and 100C, in that it includes four discrete electrodes (which will have four separate wires) with the electrodes of one arm shifted axially relative to the electrodes on the other arm, such that the electrodes of one arm are in a different axial plane than the electrodes of the other arm. As noted, this axial shift maximizes noise reduction without completely cancelling the desired recorded differential signal because of phase shift. The provision of four electrodes (which provides for focal anatomic discrimination) further enhances the SNR (signal to noise ratio).

In a further embodiment, the nerve cuff can comprise four foils/electrodes, as in cuffs 100B,C, but foils 120a,b can be axially offset from each other and foils 120c,d can be axially offset from each other, that is, the foils in one arm can be in different axial planes.

In yet a further embodiment, the nerve cuff can include three or more electrodes on each arm, with the electrodes being positioned in two or more axial planes of the nerve cuff.

As various changes could be made in the above constructions without departing from the scope of the invention, it is intended that all matter contained in the above description or shown in the accompanying drawings shall be interpreted as illustrative and not in a limiting sense. For example:

Although the preferred embodiment of the electrode assembly is as the nerve cuff 100, 100' described above, the electrode assembly could be formed an any number of different configurations, as long as it is sized to be received in the surgical site, to remain in place on the lumbar nerve during surgery, and to maintain the electrode(s) in contact with the lumbar nerve while the nerve cuff is in place.

It is preferred that the main spring be a single continuous member, the main spring could comprise a two separate springs each of which extends from beneath one ear 104 and passes through one of the arms 110.

In another alternative, the grasping arms could be omitted, as long as the nerve cuff is provided with means which enable opening of the nerve cuff to apply the nerve cuff to a nerve root. Such means could be, for example spaced apart pin holes or external axially extending channels which allow the for the nerve cuff to be grasped by a tool which can then be operated to open the nerve cuff.

These examples are merely illustrative.

The invention claimed is:

1. A nerve cuff comprising:
a body having a base and first and second arms extending from opposite sides of the base;
said base and arms being formed from an electrically insulating material; the base and first and second resilient arms defining an inner surface adapted to face a nerve when in use; said arms each comprising a fixed end adjacent said base and a free end remote from said base; said arms and/or base being sized so as to be flexible such that said nerve cuff is moveable between a relaxed position and an open position, wherein in said open position, said arms define a gap between their free ends adapted to fit over a nerve root; said body defining an axis extending through an approximate center of said base and said gap, said body having a radial width measured along an axial plane which passes through said arms and an axial width measured in a plane that is generally perpendicular to said radial width;
an elongate first electrode positioned on and extending along an inner surface of said first arm and an elongate second electrode positioned on and extending along an inner surface of said second arm; said electrodes each comprising an elongate electrically conductive foils; each said foil having a first end, a second end and side edges extending between said first and second ends, said side edges being longer than said ends; said first end of each foil being fastened to said body at a first point proximate said axis and a second end fastened to said body at a second point remote from said first point sufficient for said conductive foils to define an arc of between 120° and 140° and; said foils being secured to said body at only said first and second ends of said foils; said foils being electrically isolated from each other, wherein the inner surface of said arms is sized and shaped to maintain said at electrodes in electrical communication with the nerve root when said nerve cuff is in its closed position.

2. The nerve cuff of claim 1 wherein said first and second electrodes comprise platinum.

3. The nerve cuff of claim 1 wherein said inner surface of said body defines an arc of at least 270°.

4. The nerve cuff of claim 1 wherein said arms have an annular width of about 1-3 mm.

5. The nerve cuff of claim 1 wherein said body defines an inner diameter of 3-10 mm.

6. The nerve cuff of claim 1 further comprising a main spring contained within at least said first and second arms.

7. The nerve cuff of claim 6 wherein said main spring comprises a single spring extending through said base and into said first and second arms.

8. The nerve cuff of claim 6 comprising an electrical insulator positioned between said electrodes and said main spring to electrically insulate the electrodes from the main spring.

9. The nerve cuff of claim 8 wherein said electrical insulator has an axial width equal to or greater than an axial width of said main spring.

10. The nerve cuff of claim 9 wherein said electrical insulator comprises a polymer layer, applied to at least the inner surface of said main spring, and wherein said insulating layer optionally covers free ends of said main spring and a portion of an outer surface of the main spring at ends of the main spring.

11. The nerve cuff of claim 8 wherein said main spring comprises a leaf spring.

12. The nerve cuff of claim 6 further including first and second spaced apart grips extending from opposite sides of said base; said grips being positioned on said base, such that by urging said grips together toward each other, said nerve cuff will be moved from its relaxed position to its open position.

13. The nerve cuff of claim 12 wherein said grips are sized and shaped such that the distance between outer surfaces of said grips is less than, or equal to, the side-to-side width of said body.

14. The nerve cuff of claim 12, wherein the nerve cuff includes a grip spring member extending internally of each of said grips, wherein each said grip spring is fixed to said main spring.

15. The nerve cuff of claim 1 further comprising at least one first electrical wire in electrical communication with said at least one first electrode and at least one second electrical wire in electrical communication with said at least one second electrode; said at least one first and second electrical wires extending from said nerve cuff and being adapted to be electrically connected to a signal monitor to place said first and second electrodes in electrical communication with said signal monitor.

16. The nerve cuff of claim 15 further including a first connector at an end of first wire and a second connector at an end of said second wire, said first and second connectors being color coded; wherein said nerve cuff includes indicia associated said first electrode indicating the which of said first and second connectors is electrically connected to said first electrode.

17. The nerve cuff of claim 1 wherein said nerve cuff is sufficiently flexible such that a nerve surrounded by said nerve cuff can pop out of said nerve cuff through said gap if said nerve cuff is dislodged.

18. The nerve cuff of claim 1 wherein at least said arms are formed from 80 durometer silicone.

19. A nerve cuff comprising:
a body having a base and first and second arms extending from opposite sides of the base; said base and arms being formed from an electrically insulating material; the base and first and second arms defining an inner surface adapted to face a nerve when in use; said arms each comprising a fixed end adjacent said base and a free end remote from said base; said arms and/or said base being sized so as to be flexible such that said nerve cuff is moveable between a relaxed position and an open position, wherein in said open position, said arms define a gap between their free ends adapted to fit over a nerve root; said body having a radial width measured along an axial plane which passes through said arms and an axial width measured in a plane that is generally perpendicular to said radial width;
a main spring contained within at least said first and second arms;
a first electrode positioned on an inner surface of said first arm and a second electrode positioned on an inner surface of said second arm; said electrodes each comprising elongate electrically conductive foils which define arcs of between about 120° and 140°; said foils being electrically isolated from each other, and
an insulator layer positioned between said main spring and said first and second electrodes, said insulating layer having a length at least equal to a length of said first and second electrodes whereby said main spring is electrically isolated from said electrodes;
wherein the inner surface of said arms is sized and shaped to maintain said at electrodes in electrical communication with the nerve root when said nerve cuff is in its closed position.

20. A nerve cuff adapted to fit about a lumbar nerve; the nerve cuff comprising:
a body having a base and first and second arms extending from opposite sides of the base; said base and arms being formed from an electrically insulating material; the base and first and second arms defining an inner surface adapted to face a nerve when in use; said arms each comprising a fixed end adjacent said base and a free end remote from said base; said arms and/or base being sized so as to be flexible such that said nerve cuff is moveable between a relaxed position and an open position, wherein in said open position, said arms defining a gap between their free ends adapted to fit over a nerve root; said body having a radial width measured along an axial plane which passes through said arms and an axial width measured in a plane that is generally perpendicular to said radial width;
at least one first electrode positioned on an inner surface of said first arm and at least one second electrode positioned on an inner surface of said second arm; said electrodes each comprising electrically conductive foils; said foils being electrically isolated from each other;
first and second spaced apart grips extending from opposite sides of said base; said grips being positioned on said base, such that by urging said grips together toward each other, said nerve cuff will be moved from its relaxed position to its open position; said grips being sized and shaped such that the distance between free ends of outer surfaces of said grips is less than, or equal to, a widest radial width of said nerve cuff,
a main spring member extending through said body and said first and second arms and a grip spring in each of said grips; wherein said main spring and said grip springs are internal of said nerve cuff; each grip spring comprising an arm portion extending from said main spring member into said grip and foot portion extending along a portion of said main spring member; said foot portion of said grip spring being fixed to said main spring;

wherein the inner surface of said arms is sized and shaped to maintain said at electrodes in electrical communication with the nerve root when said nerve cuff is in its closed position.

21. The nerve cuff of claim 20 wherein said each arm comprises one electrode, and wherein the electrodes of said first and second arms are positioned in a common axial plane or are positioned in different axial planes.

22. The nerve cuff of claim 20 wherein each said arm comprises two or more electrodes, and wherein the electrodes of said first arm are positioned in a common axial plane or are positioned in different axial planes with the electrodes of said second arm.

23. The nerve cuff of claim 22 wherein the two or more electrodes of a single arm are all positioned in the same axial plane or are positioned in different axial planes.

* * * * *